US011878136B2

(12) United States Patent
Giraud et al.

(10) Patent No.: US 11,878,136 B2
(45) Date of Patent: Jan. 23, 2024

(54) MEDICAMENT DELIVERY DEVICE AND METHOD OF USING AND MAKING SAME

(71) Applicant: CSP TECHNOLOGIES, INC., Auburn, AL (US)

(72) Inventors: Jean-Pierre Giraud, Auburn, AL (US); Franklin Lee Lucas, Jr., Auburn, AL (US); Bruce Rabinne, Boissy-le-Chatel (FR)

(73) Assignee: CSP TECHNOLOGIES, INC., Auburn, AL (US)

( * ) Notice: Subject to any disclaimer, the term of this patent is extended or adjusted under 35 U.S.C. 154(b) by 714 days.

(21) Appl. No.: 16/949,458

(22) Filed: Oct. 29, 2020

(65) Prior Publication Data

US 2021/0038875 A1 Feb. 11, 2021

Related U.S. Application Data

(63) Continuation of application No. PCT/US2019/030145, filed on May 1, 2019.

(60) Provisional application No. 62/693,438, filed on Jul. 2, 2018, provisional application No. 62/665,485, filed on May 1, 2018.

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01); *A61M 2037/0053* (2013.01)

(58) Field of Classification Search
None
See application file for complete search history.

(56) References Cited

U.S. PATENT DOCUMENTS

| 5,911,937 | A  | 6/1999  | Hekal          |
|-----------|----|---------|----------------|
| 6,080,350 | A  | 6/2000  | Hekal          |
| 6,124,006 | A  | 9/2000  | Hekal          |
| 6,130,263 | A  | 10/2000 | Hekal          |
| 6,174,952 | B1 | 1/2001  | Hekal          |
| 6,214,255 | B1 | 4/2001  | Hekal          |
| 6,221,446 | B1 | 4/2001  | Hekal          |
| 2002/0091357 | A1 | 7/2002 | Trautman et al. |
| 2002/0120236 | A1 | 8/2002 | Diaz et al.    |
| 2005/0261631 | A1 | 11/2005 | Clarke et al. |
| 2011/0112484 | A1 | 5/2011 | Carter et al.  |
| 2013/0296803 | A1 | 11/2013 | Kriesel       |

(Continued)

FOREIGN PATENT DOCUMENTS

| CN | 1479589 A | 3/2004  |
|----|-----------|---------|
| CN | 1691969 A | 11/2005 |

(Continued)

OTHER PUBLICATIONS

International Search Report for International Application No. PCT/US2019/030145, dated Sep. 26, 2019.

*Primary Examiner* — Manuel A Mendez
(74) *Attorney, Agent, or Firm* — Mark T. Vogelbacker; Eckert Seamans Cherin & Mellott, LLC

(57) ABSTRACT

A system, apparatus and method for a tightly sealed, low moisture vapor transmission, low relative humidity headspace atmosphere aseptic vaccine delivery with low particulate generation. The system can include a housing, desiccant and a biasing member designed to quickly and efficiently deliver medicament to a patient.

23 Claims, 22 Drawing Sheets

(56) References Cited

U.S. PATENT DOCUMENTS

2016/0039955 A1    2/2016  Kibele et al.
2018/0015271 A1*   1/2018  Junger .............. A61M 37/0015

FOREIGN PATENT DOCUMENTS

| CN | 1886319 A | 12/2006 | | |
|---|---|---|---|---|
| CN | 103908708 A | 7/2014 | | |
| WO | WO-2005039685 A1 * | 5/2005 | ............. | A61K 31/00 |
| WO | 2015168219 A1 | 11/2015 | | |
| WO | 2016/123665 A1 | 8/2016 | | |
| WO | 2018/075851 A2 | 4/2018 | | |

* cited by examiner

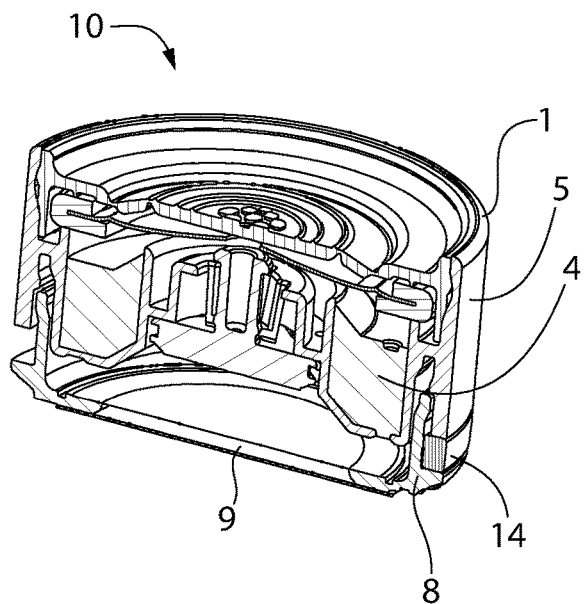
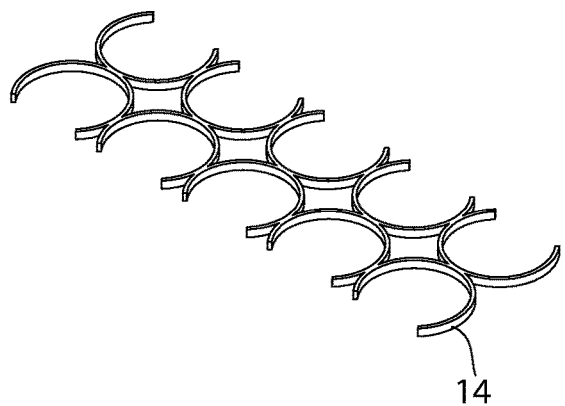
FIG. 6A    FIG. 6B
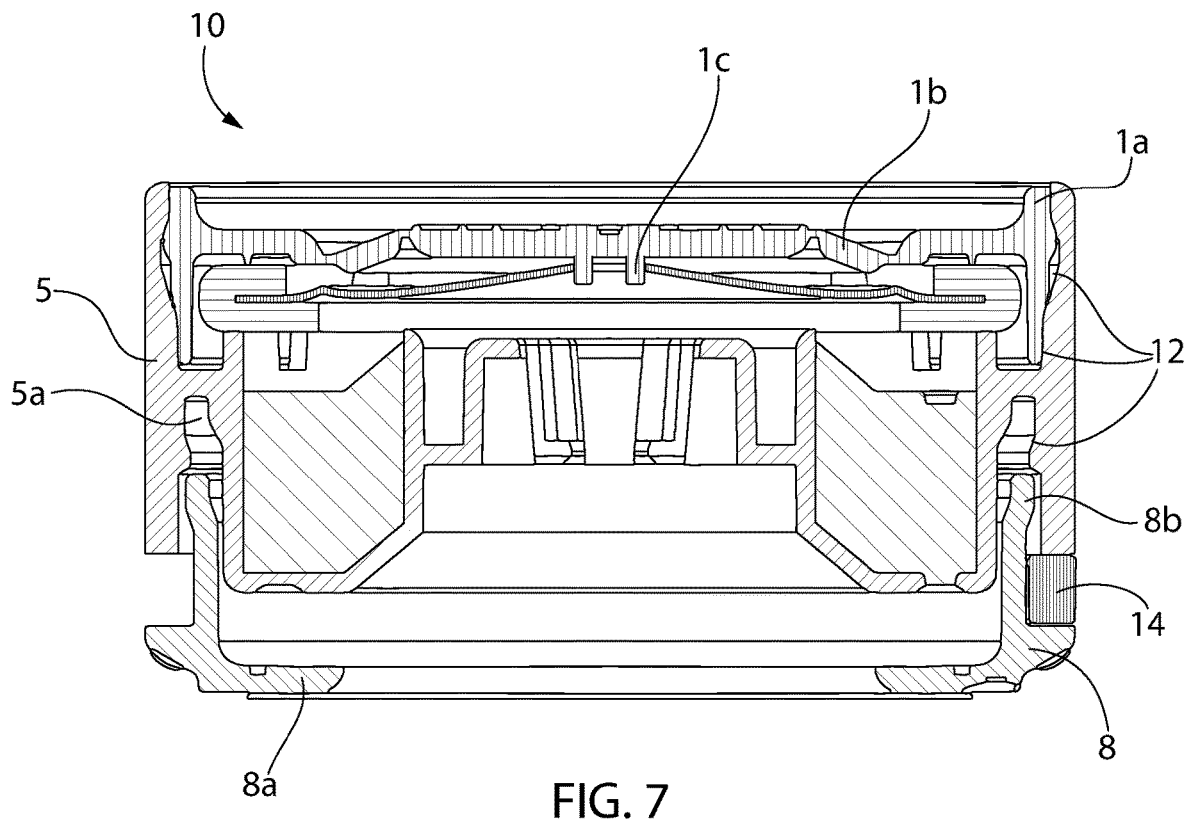
FIG. 7

MEDICAMENT DELIVERY DEVICE AND METHOD OF USING AND MAKING SAME

CROSS-REFERENCE TO RELATED APPLICATIONS

The present application is a continuation of International Application No. PCT/US2019/030145, filed May 1, 2019 and titled "MEDICAMENT DELIVERY DEVICE AND METHOD OF USING AND MAKING SAME," which claims priority to U.S. Provisional Application No. 62/693,438, filed Jul. 2, 2018 and tiled "MEDICAMENT DELIVERY DEVICE AND METHOD OF USING AND MAKING SAME," and U.S. Provisional Application No. 62/665,485, filed May 1, 2018 and titled "MEDICAMENT DELIVERY DEVICE AND METHOD OF USING AND MAKING SAME," the subject matter of each being hereby incorporated by reference in its entirety.

FIELD

The presently disclosed technology relates generally to medicament delivery systems and methods of using, assembling and making same. More particularly, one optional aspect of the presently disclosed technology relates to a final product that is a tightly sealed, low moisture vapor transmission, low relative humidity headspace atmosphere aseptic vaccine delivery system with low particulate generation.

BACKGROUND AND DESCRIPTION OF RELATED ART

There are a variety of known systems and methods to inject or otherwise deliver medicament(s) to a patient, such as those described and claimed in International Publication No. WO 2016/123665 (Junger), which is hereby incorporated by reference. Each of these systems or methods can be beneficial. However, there remain difficulties with the prior art designs, evident during molding, creation or production, as well as accidental engagement or activation, moisture build-up, gas passage therethrough and sterilization thereof.

BRIEF SUMMARY

Embodiments of the presently disclosed technology overcome certain drawbacks of prior art designs and satisfy the above-outlined and other objectives.

In one aspect, a device contains three phase polymer technology loaded with a four angstrom (4 A) molecular sieve. Optionally, the device can be formed utilizing multi-shot injection molding or overmolding combined with film membrane cutting via laser and post mold assembly, with low particulate generation. In an optional aspect, the device can contain approximately 1-2 engineered tight interference fit seals to provide a moisture vapor transmission rate (MVTR) of less than approximately 500 micrograms per day into the device. In any embodiment, the device can incorporate a double snap fit system, wherein the first snap can be designed to be an intermediate position and the second snap can be designed for a permanent closed position, thus keeping the two parts of the device a single unit for packaging and transport, opening both parts to insert product, and terminally closing and sealing.

In one aspect, the device can mechanically protect the inner mechanisms and product while contributing to the sterile and moisture ingress barrier of the primary packaging. Optionally, the device can include a membrane that is smooth, biocompatible, sustains sterilization, and will remain in tension throughout normal use of the device. In any embodiment, the device can house a membrane in the range of 10+/−5 μm. In any embodiment, the device can utilize a flexible member or biasing member (e.g., a spring formed of metal) that can be overmolded into a polymeric part, thereby mechanically mating the biasing member and the plastic part together. The wall thickness of the polymeric part can be optimized so that when overmolded and mechanically bonded will still generate a spring trigger force of approximately 20-50 Newtons.

Optionally, the device is design for a single use, such that it is intended to be discarded after one use.

BRIEF DESCRIPTION OF SEVERAL VIEWS OF THE DRAWINGS

The foregoing summary, as well as the following detailed description of the invention, will be better understood when read in conjunction with the appended drawings, wherein like numerals designate like elements throughout. For the purpose of illustrating the invention, there are shown in the drawings various illustrative embodiments. It should be understood, however, that the presently disclosed technology is not limited to the precise arrangements and instrumentalities shown. In the drawings:

FIG. 6A is a cross-sectional perspective view of the system of FIG. 1, taken along line A-A in FIG. 1;

FIG. 6B is a perspective view of a plurality of connected spacers;

FIG. 7 is a cross-sectional side elevation view of the system shown in FIG. 1, taken along line A-A in FIG. 1, in a partially assembled configuration, wherein three contact surfaces are identified that provide limited and controlled fluid ingress

DETAILED DESCRIPTION

Figure 1:
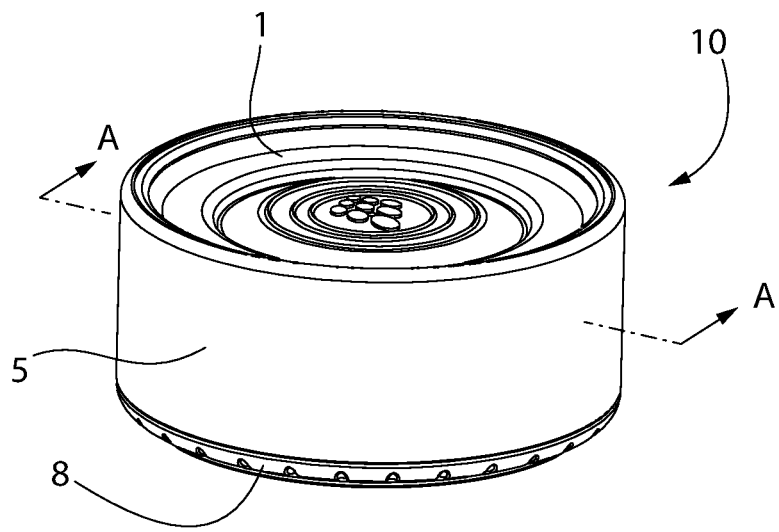
FIG. 1 is a top perspective view of a medicament delivery system according to an embodiment of the presently disclosed technology.

While systems, devices and methods are described herein by way of examples and embodiments, those skilled in the art recognize that the systems, devices and methods of the presently disclosed technology are not limited to the embodiments or drawings described. It should be understood that the drawings and description are not intended to be limited to the particular form disclosed. Rather, the intention covers all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to. Unless specifically set forth herein, the terms "a," "an" and "the" are not limited to one element but instead should be read as meaning "at least one." The terminology includes the words noted above, derivatives thereof and words of similar import.

Referring to the drawings in detail, wherein like numerals indicate like elements throughout, FIGS. 1-11 illustrate an optional embodiment of a system or device ("system" and "device" are used herein interchangeably), generally designated 10, and aspects thereof. The device 10 is an optimized, differentiated cannula-free, needle-free vaccine delivery assembly that preferably provides a low relative humidity internal atmosphere for protection of moisture-sensitive medicament products. Optionally, in any embodiment, the presently disclosed technology is an easy-to-fill design that is provided to a medicament supplier or aseptic filler as a single unit and in an intermediate position for removable attachment to a membrane ring or locker. Optionally, in any embodiment, the aseptic filler can remove the membrane ring, place product (e.g., the drug(s) to be administered, a patch holder, or approximately 500-1,000 micro needles) into the device 10, then place the membrane ring into a permanent closed position, thereby terminally closing and sealing the device and preparing the device for eventual delivery of medicament to an individual. The presently disclosed technology also provides methods for producing and/or assembling the system or device as to provide the aseptic filling operation or automation.

Optionally in any embodiment, the design provides an optimized polymeric wall thickness to accommodate, house and/or bond a metal spring to generate a spring force of approximately 20-50 Newtons. Optionally in any embodiment, the design provides a low relative humidity internal atmosphere in the device for protecting moisture sensitive products while providing engineered interference friction fit polymeric seals to ensure that the device, when sealed, is moisture tight. The term "moisture tight" with respect to the device is a moisture ingress rate of less than 1500 micrograms per day, at ambient conditions of 80% relative humidity and 22.2° C., optionally less than 1000 micrograms per day, optionally less than 750 micrograms per day, optionally less than 500 micrograms per day, optionally from 50-1000 micrograms per day, optionally from 50-500 micrograms per day, all at the aforementioned ambient conditions.

Optionally, the device 10 is designed to apply or administer a drug-containing patch to an individual. The patch, when actuated (e.g., by a spring and/or a user), can penetrate the individuals' epidermis to the desired depth and deliver the medicament or one or more therapeutically effective active pharmaceutical ingredients. Optionally in any embodiment, the patch can be a high-density array (2.5-10 k/cm$^2$) of projections that puncture through the epidermis, after which a dried vaccine coating formulation is rapidly removed from its surface. The device 10 maintains the sterility and performance of the product or medicament over its shelf life, for example by maintaining a low level of moisture in the device 10. The device 10 is designed to withstand transport, storage and/or use with no damage to the medicament. The device 10 is intuitive for an individual to use and occupies a relatively small amount of space.

Figure 3:
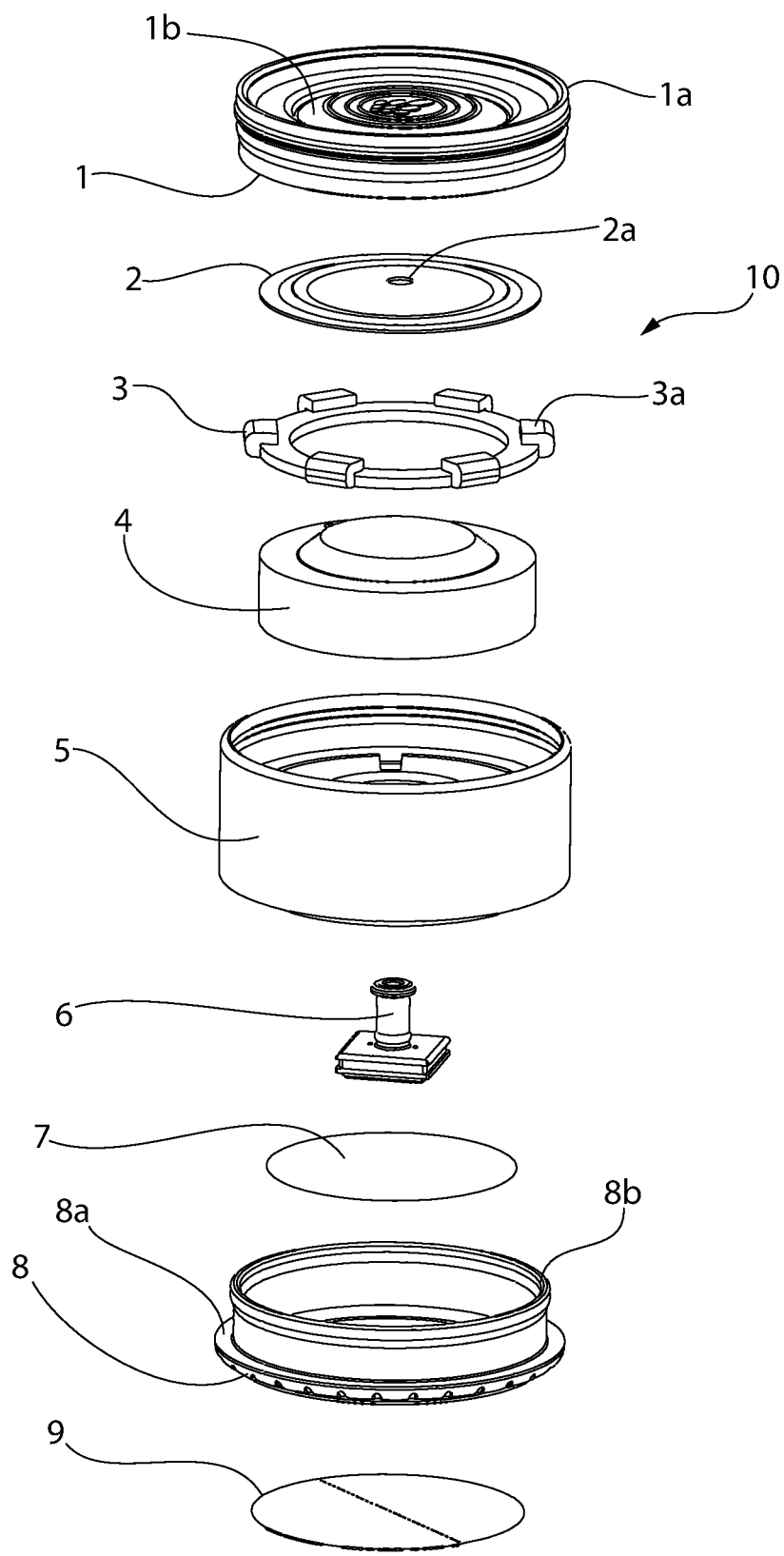
FIG. 3 is a partially exploded top perspective view of the system shown in FIG. 1.
Figure 4A:
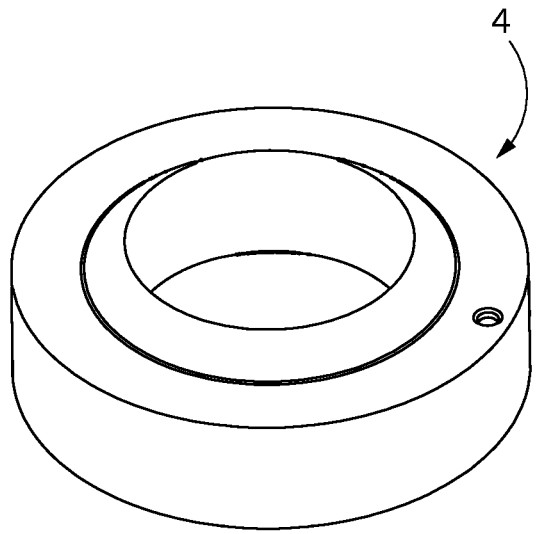
FIG. 4A is a top perspective view of one embodiment a component of the system shown in FIG. 3.
Figure 4B:
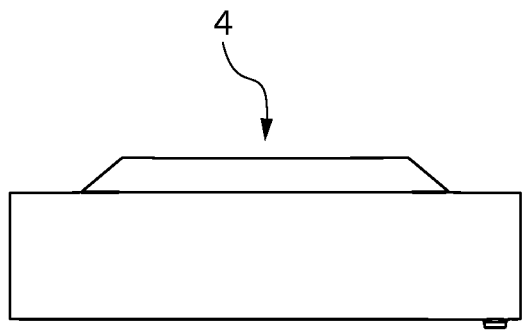
FIG. 4B is a side elevation view of the component shown in FIG. 4A.
Figure 5:
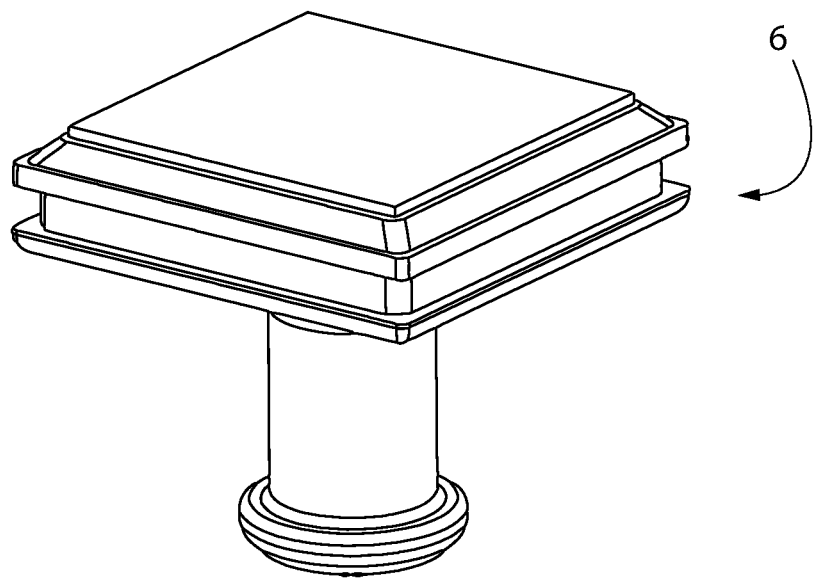
FIG. 5 is a bottom perspective view of one embodiment of another component of the system shown in FIG. 3.
Figure 8:
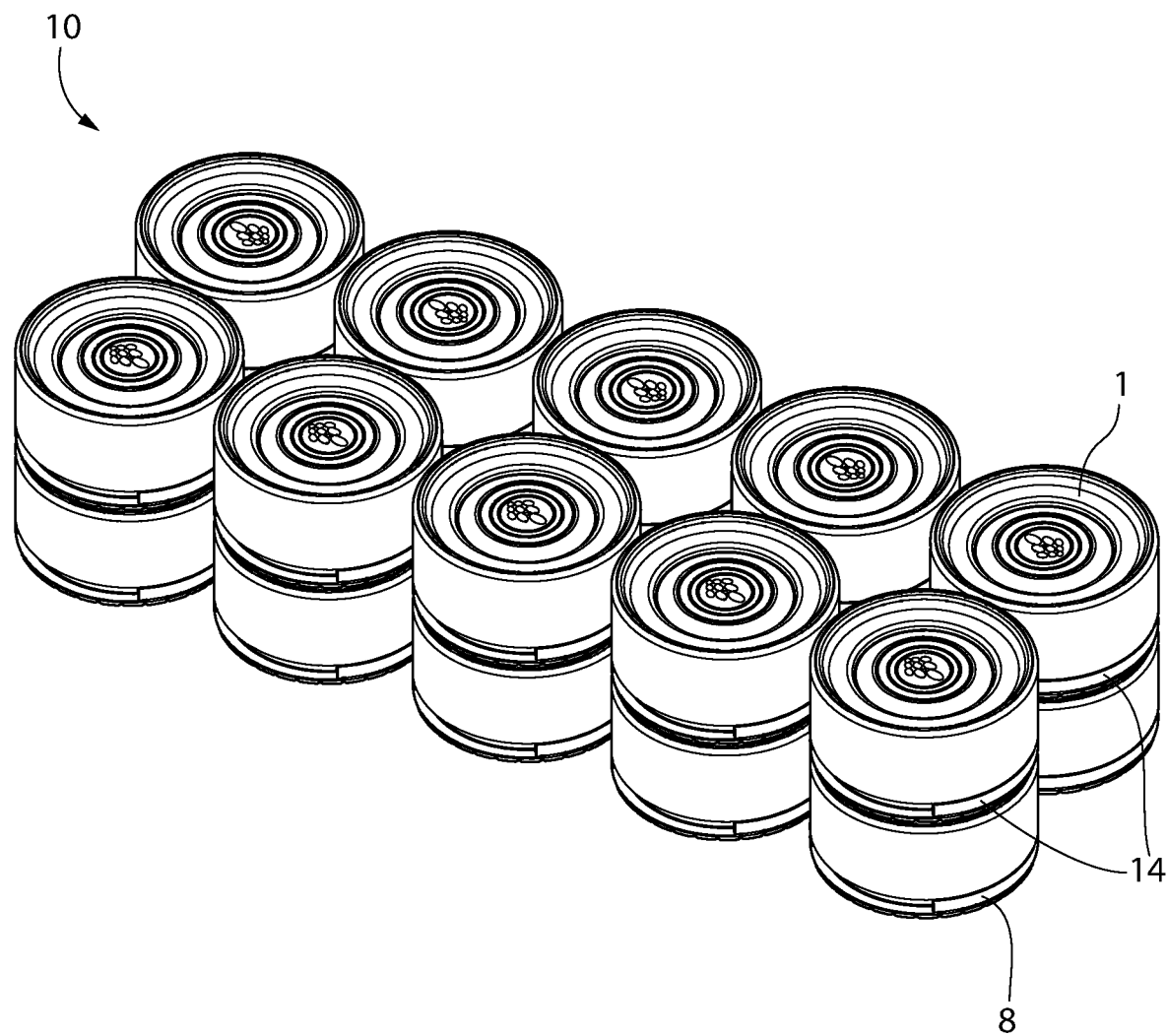
FIG. 8 is a top perspective view of two rows and two columns of systems shown in FIG. 1 attached to two sets of the plurality of connected spacers shown in FIG. 6B.

As shown in FIG. 3, in one optional embodiment, the device 10 includes a plurality of components designed to be easily assembled, sterilized, and/or to easily deliver medicament to a patient. In particular, the device 10 can include one or more of the following: a top or actuator 1, a biasing member or spring 2, an optional ring 3, a desiccant 4 (e.g., in the form of a desiccant entrained polymer), a patch holder or housing 5, a patch 6, a membrane 7, a membrane assembly or locker 8, and/or a seal 9. Optionally, two or more of the devices 10 can be vertically stacked (see, e.g., FIG. 8) for assembly, production, storage and/or transport purposes.

Figure 10:
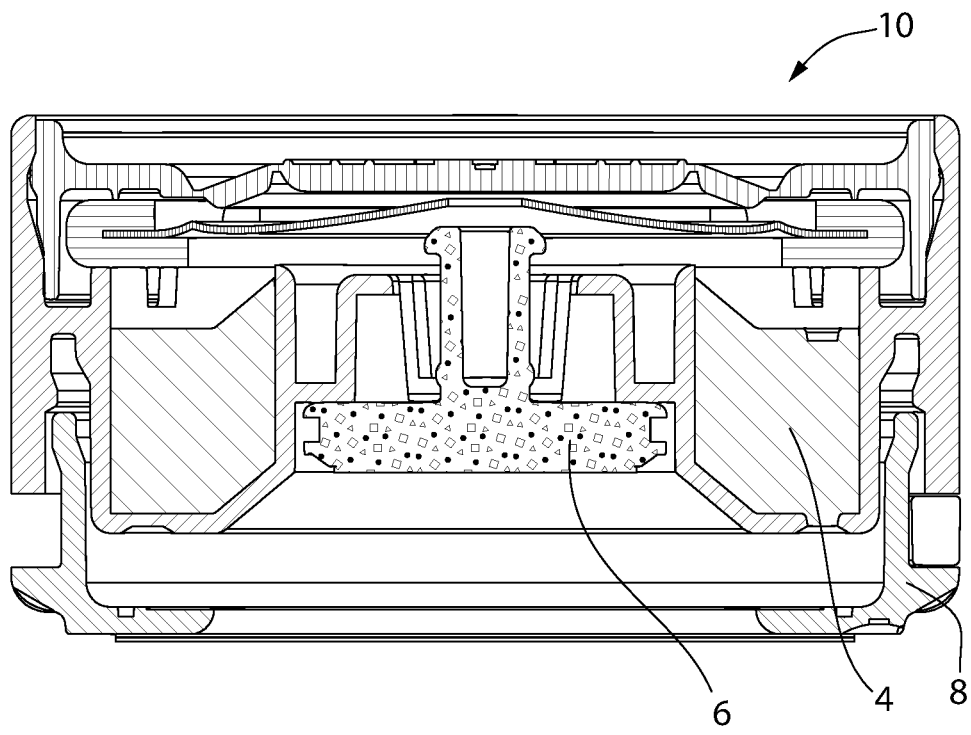
FIG. 10 is a cross-sectional, side elevation view of the system shown in FIG. 1 in a non-activated or shelf-life configuration.

Optionally, a raised rib or lip 1a can extend around an entire periphery of the actuator 1. The actuator 1 can include a deflectable portion 1*b* that allows at least a central portion of the actuator 1 to move with respect to the raised rib 1*a*. Optionally, the deflectable portion 1*b* can be attached to other portions (or a reminder) of the actuator 1 by one or more spaced-apart and/or concentric living hinges 1*d* (see FIG. 11), for example. Thus, as an optional feature that may be used in any embodiment, the actuator 1 can provide a visual indication to the user when the system 10 is ready-to-be activated or has been activated. As shown in FIG. 7, a lower or bottom surface of the actuator 1 can include a projection 1*c* extending downwardly or outwardly therefrom. However, as shown in FIG. 10, the actuator 1 is not required to include the projection 1*c*.

Optionally in any embodiment, such as the one shown here, the biasing member 2 can be in the shape of a dome. Alternatively, the biasing member 2 can be in the shape of a cone. At least one or more portions of an outer periphery of the biasing member 2 can be surrounded by a portion of the ring 3. More particularly, one or more spaced-apart engagement hooks 3*a* can be positioned at or near an outer periphery of the ring 3 and can be sized, shaped and/or configured to receive at least a portion of an outer periphery of the biasing member 2 therein. When attached or connected to the ring 3, the biasing member 2 can be movable or deflectable between an upper, non-engaged or concave position (see FIGS. 9 and 10) and a lower, engaged or convex position (see FIG. 11). Thus, the biasing member 2 acts as a spring. As shown in FIG. 3, the biasing member 2 can also include a central opening 2*a* that is sized and shaped to receive and engage at least a portion of the projection 1*c* of the actuator 1 therein.

The geometry and/or components of the system 10 prevent or at least reduce the likelihood of accidental engagement or activation. More particularly, the size, shape and/or configuration of one or more of the components of the system 10 described herein require a certain amount or degree of flex to cause or effectuate activation of the medicament delivery. Thus, the system 10 is designed to reduce the likelihood of accidentally or unintentionally flexing or otherwise setting-off the biasing member 2.

The desiccant 4 can be in the form of a donut or ring. The desiccant 4 can surround at least a portion of the patch 6 and fit entirely within the holder 5. Optionally, an interior surface of the desiccant 4 can have one or more ribs to increase the friction between the desiccant 4 and the holder 5. Optionally, the size, shape and/or configuration of the desiccant 4 can contribute to the rigidity or strength of the device 10.

The desiccant 4 can be any of those developed or manufactured by CSP Technologies of Auburn, Ala. Optionally, the desiccant 4 is in the form of a desiccant entrained polymer. Optionally, a desiccant entrained polymer may be produced as two primary components (i.e., a two phase polymer)—a base polymer and an active agent. In another embodiment, a desiccant entrained polymer may be produced as at least three primary components (i.e., a three phase polymer). U.S. Pat. Nos. 5,911,937, 6,214,255, 6,130,263, 6,080,350, 6,174,952, 6,124,006, and 6,221,446, and U.S. Pat. Pub. No. 2016/0039955, which are all incorporated by reference herein in their entireties, describe three phase entrained polymers and methods for making the same. For example, a three phase desiccant polymer may include a base polymer (e.g., polypropylene, polyethylene or mixtures thereof), a desiccant material (e.g., molecular sieve or silica gel) and a channeling agent (e.g., ethylene-vinyl alcohol (EVOH), polyvinyl alcohol (PVOH) or polyethylene glycol (PEG)). The channeling agent may form passages in the three phase polymer through which moisture is communicable to a desiccating agent entrained within the polymer. Optionally, in a three phase desiccant entrained polymer, the base polymer is present in an amount of 24% to 60% by weight, the desiccant is present in an amount of 40% to 70% by weight and the channeling agent is present in an amount of 2% to 15% by weight. Optionally, the desiccant 4 can be protected by packaging the system(s) 10 into a foil sealed bag upon initial assembly and not opened until the system(s) 10 arrive(s) at the sterilization and aseptic filling destination. Optionally, the desiccant 4 can weigh 4.60 grams, or approximately 400-700 grams.

Optionally in any embodiment, the desiccant 4 is partially or completely formed of the following components: (i) a base resin, (ii) optionally a channeling agent, and (iii) a desiccant material, such as but not limited to molecular sieve. In one embodiment, the resin is a transparent polypropylene (PP) random coplymer, which can be modified with a nucleating agent. In any embodiment, the resin can be any resin that demonstrates easy processability, high transparency, high gloss and/or a good stiffness-impact balance. Optionally, the resin can be PP Bormed RF830MO, produced by Borealis, optionally in an amount of approximately 23%. Optionally, the channeling agent can be PEG 4000S Clariant, optionally in an amount of approximately 8%. Optionally, the molecular sieve can be Molecular Sieve 4A, optionally in an amount of 69%.

As one example, the desiccant 4 can be formed of approximately 23% by weight of PP Bormed RF830MO, approximately 8% by weight of PEG 4000S Clariant, and approximately 69% by weight of Molecular Sieve 4A. This material composition can be sterilized with a gas (such as ethylene oxide (ETO)) and/or steam. This compound or material composition has been tested to be well suited to sterilization at least because of the grade of PP used. The results of such testing showed no deterioration of adsorption performance or discoloration due to sterilization. In one embodiment, the desiccant is designed with 616 mg of moisture capacity and configured to accommodate an ingress of 540 µg/day at ambient conditions of 80% relative humidity and 22.2° C., based on a projected shelf life.

Optionally, the patch 6 can be a microprojection array, a microarray patch, or a microarray needle. Optionally, the patch 6 can include approximately 500-1,000 micro needles. At least a lower or bottom portion of the membrane 7 can contact the skin, for example, of a patient during operation or administration. However, the bottom portion of the membrane 7 is optionally prevented from contacting the patient's skin until the seal 9 is removed from the membrane assembly 8.

Figure 11:
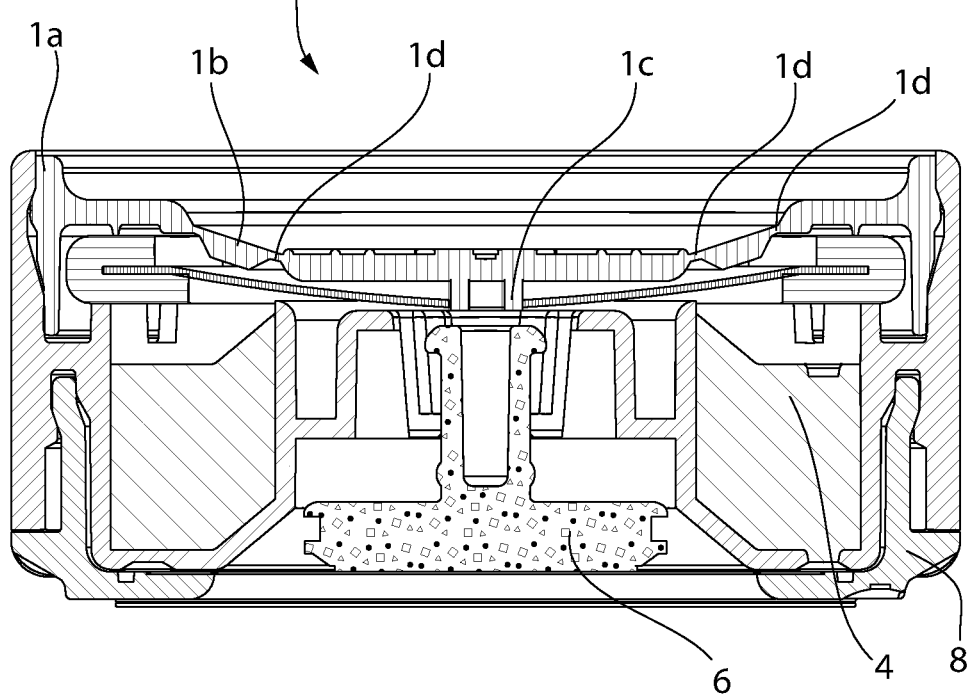
FIG. 11 is a cross-sectional, side elevation view of the system shown in FIG. 1 in an activated or pushed configuration.

One or more components of the device 10 can be moveable or reconfigurable between a non-activated, stackable, or shelf life configuration (see FIG. 10) and an activated or push configuration (see FIG. 11). Optionally in any embodiment, the non-activated configuration is used for storage (e.g., stacking) and transport of the system(s) 10. Optionally, in such a configuration, one or more of the systems 10 can be stored in an aluminum (e.g., foil) bag or container. The activated configuration can be used to deliver medicament to a patient. Optionally, once the system 10 is moved from the non-activated configuration to the activated configuration, or the medicament is otherwise delivered, the system can be discarded (e.g., the device is one-use or disposable).

Figure 2:
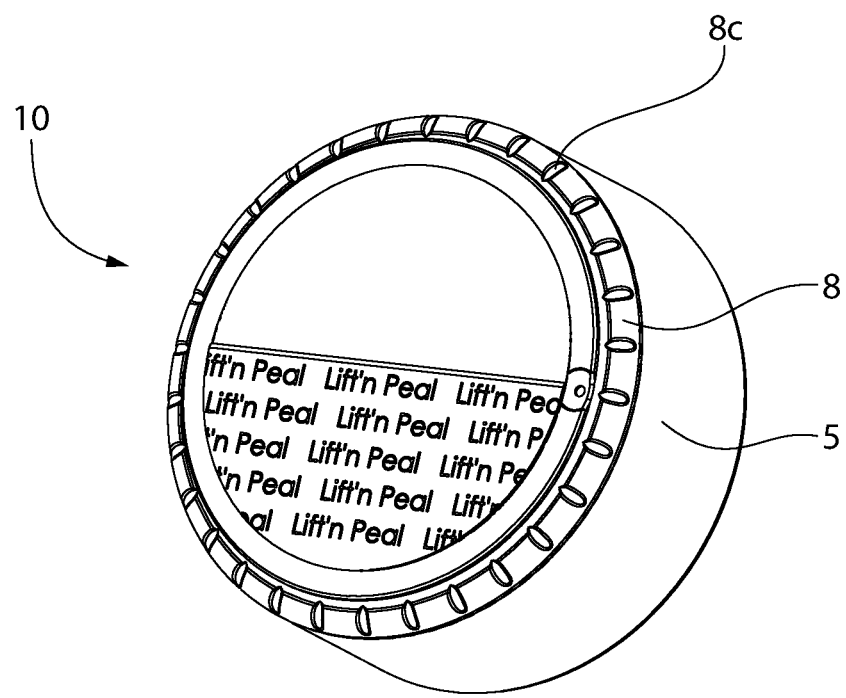
FIG. 2 is a bottom perspective view of the system shown in FIG. 1.

As shown in FIG. 3, the membrane assembly 8 can include a base wall 8*a* and a side wall 8*b* extending upwardly, outwardly and/or perpendicularly therefrom. Optionally, as shown in FIG. 2, a plurality of spaced-apart serrations or grooves 8*c* can be located around or near an outer periphery of the membrane locker 8 on the base wall 8a thereof. The serrations 8c can allow the passage of fluid (e.g., gas or air) therethrough when two systems 10 are vertically stacked. The membrane assembly 8 can be movable with respect to the housing 5, for example along a longitudinal axis L of the housing 5, between a first or spaced-apart configuration (FIG. 9) and a second or fully engaged configuration (FIGS. 10 and 11). More specifically, in any embodiment, at least a portion of the side wall 8b of the membrane assembly 8 can extend into a slot or receptacle 5a (see FIG. 7) of the housing 5. Optionally, the seal 9 can be a foil cover and/or a lift-and-peel cover.

As shown in FIGS. 6A-9, the system 10 can include and/or utilize one or more spacers 14. As shown in FIG. 6B, each spacer 14 can, optionally, be arcuate in shape (at least in one plane) to match the outer or side wall contour of the system 10, the housing 5, and/or the membrane assembly 8. More specifically, each spacer 14 can have a circular or semi-circular shape. Multiple spacers 14 can be attached together so as to connect multiple systems 10.

Optionally in any embodiment, prior to insertion of the patch 6 into the housing 5 and/or the system 10, at least a portion of a spacer 14 is positioned at or beneath at least a portion of a bottom edge surface of the housing 5. In this configuration, the spacer 14 can serve to maintain a sufficient or predetermined distance between the membrane assembly 8 and the housing 5 (e.g., between a tip or top of the side wall 8b of the membrane assembly 8 and an upper surface of the slot 5a of the housing 5), thereby permitting the passage of fluid (e.g., gas or air) through at least a portion of the system 10. Optionally in any embodiment, the spacer 14 prevents the membrane assembly 8 from moving to its final position against and/or with respect to the housing 5 (see FIG. 9). Optionally, the system 10 is prevented from being terminally sealed unless and until the spacer 14 is separated from the membrane assembly 8 and/or the holder 5. The spacer 14 can be removed or separated from between membrane assembly 8 and the holder 5, thereby allowing the system 10 to be terminally sealed and/or compressed or moved from the non-activated or stackable configuration to an activated or push configuration.

The presently disclosed technology includes methods for assembly or partial assembly of the system 10. Optionally, as a first step, the ring 3 can be attached to an outer periphery of the biasing member 2. Next, the actuator 1 can be attached to the combined ring 3 and biasing member 2. Optionally, the desiccant 4 can be inserted into and/or attached to the housing 5, and the combined actuator 1, biasing member 2 and ring 3 can be attached thereto. Optionally, this process can be duplicated to assemble other systems 10. Optionally, an array of spacers 14 can then be attached to the housings 5 of the systems 10, and the combined membrane assembly 8, the membrane 7 and the seal 9 can be attached to a remainder of the system 10. Optionally, these assembled components of the system 10 are presented for sterilization, such as gas sterilization, vaporized parasitic acid (VPA) sterilization, gamma sterilization, peracetic acid (PAA) and/or ethylene oxide (EO) sterilization.

In one configuration (e.g., a partially assembled state) of an optional embodiment, the system 10 is configured or structured such that fluid (e.g., gas or air) can pass therethrough and/or the system 10 can be easily sterilized by gas sterilization, e.g., EO sterilization. For example, as shown in FIG. 7, the system 10 optionally includes one or more contact surfaces 12 when two or more systems 10 are vertically stacked. The contact surfaces 12 are designed to permit limited, controlled and/or pre-defined fluid (e.g., gas or air) ingress therethrough. Optionally, the serrations 8c can work in conjunction with the contact surfaces 12 to increase the ability for fluid (e.g., gas or air) to permeate through one or more partially assembled systems 10.

Optionally, at least a portion of the system 10 can be subject to sterilization (e.g., VPA or EO) prior to being subject to aseptic filling automation. More particularly, the system 10 can be subject to VPA or EO sterilization in the two left-most configurations in FIG. 9. In any embodiment, all of the above-described components, except for the patch 6, can be presented for VPA or EO sterilization. Once those or certain components of the system(s) 10 has/have been appropriately sterilized, the patch 6 can be inserted into the housing 5 or the system 10 can otherwise be fully assembled in aseptic filling automation.

Figure 9:
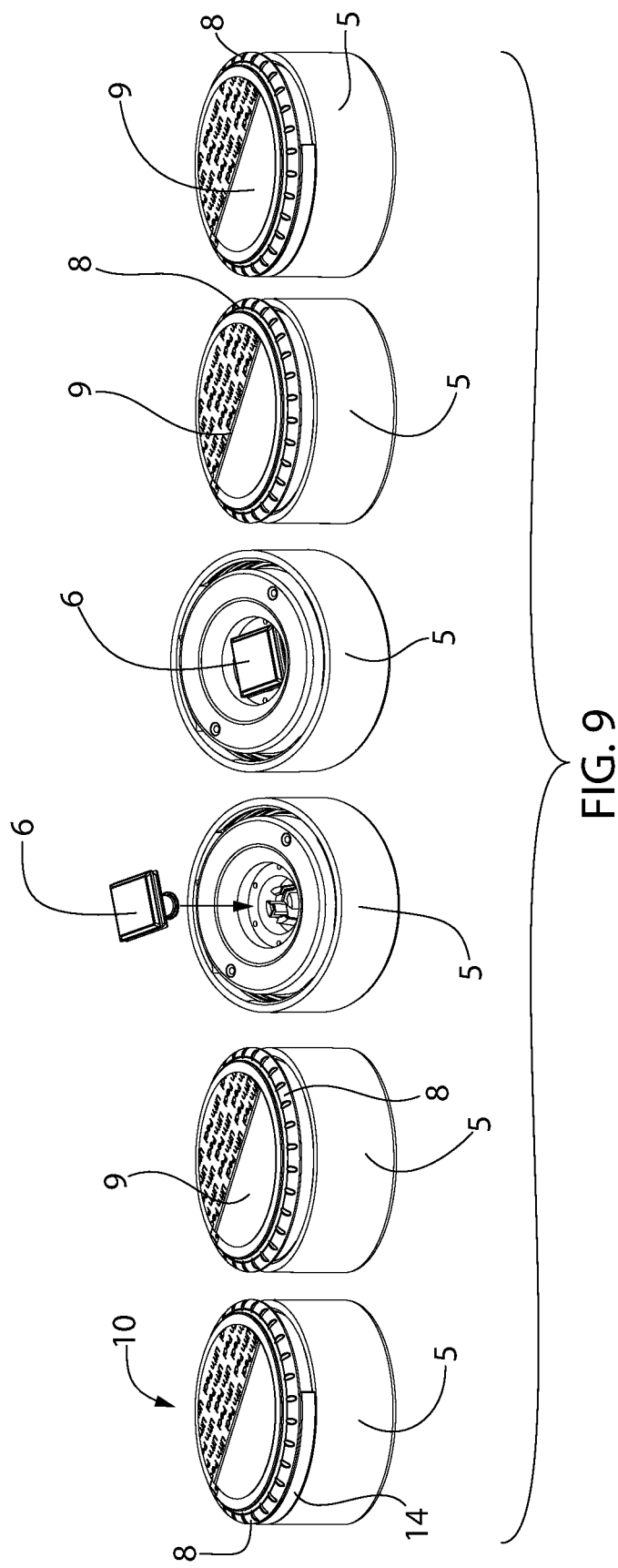
FIG. 9 shows a plurality of perspective views of various stages of assembly of the system shown in FIG. 1 according to one embodiment of the present disclosure.

FIG. 9 illustrates optional steps of a method to further assemble and/or create the system 10. For example, as shown in FIG. 9, optionally, the spacer 14 can be removed from the system 10 or otherwise separated from the membrane assembly 8 and the holder 5 before the membrane assembly 8 is separated from the remaining components of the system 10. The patch 6 can then be inserted into the housing 5. Optionally, the patch 6 can be snap-fitted into the housing 5. The membrane assembly 8 can then be reattached to the housing 5, and then pressed into the housing 5. In this configuration, once the seal 9 is removed from the membrane assembly 8, the system 10 is ready to be activated or deliver the medicament to the patient.

Figure 12:
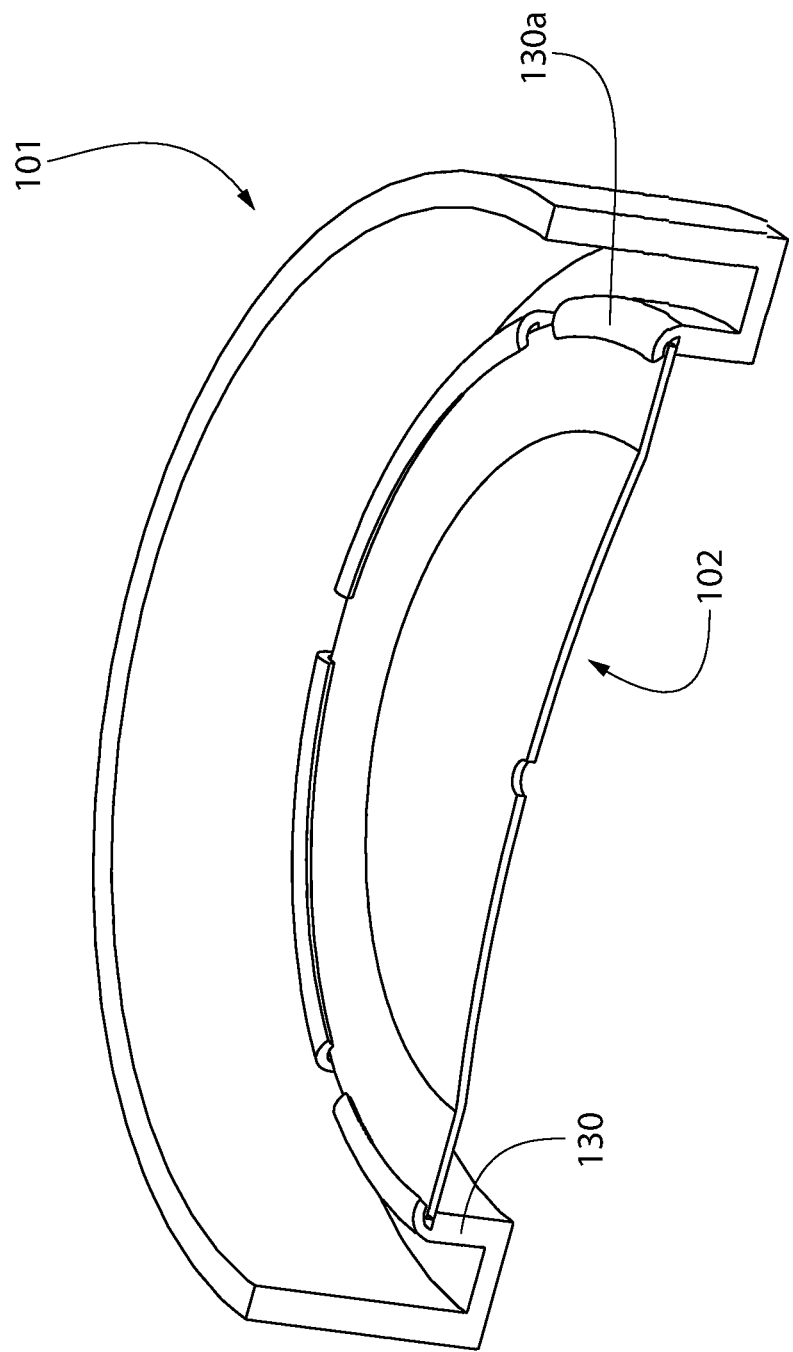
FIG. 12 is a cross-sectional perspective view of at least a portion of an actuator and a biasing member taken along line A-A of FIG. 1, according to one embodiment of the presently disclosed technology.
Figure 13:
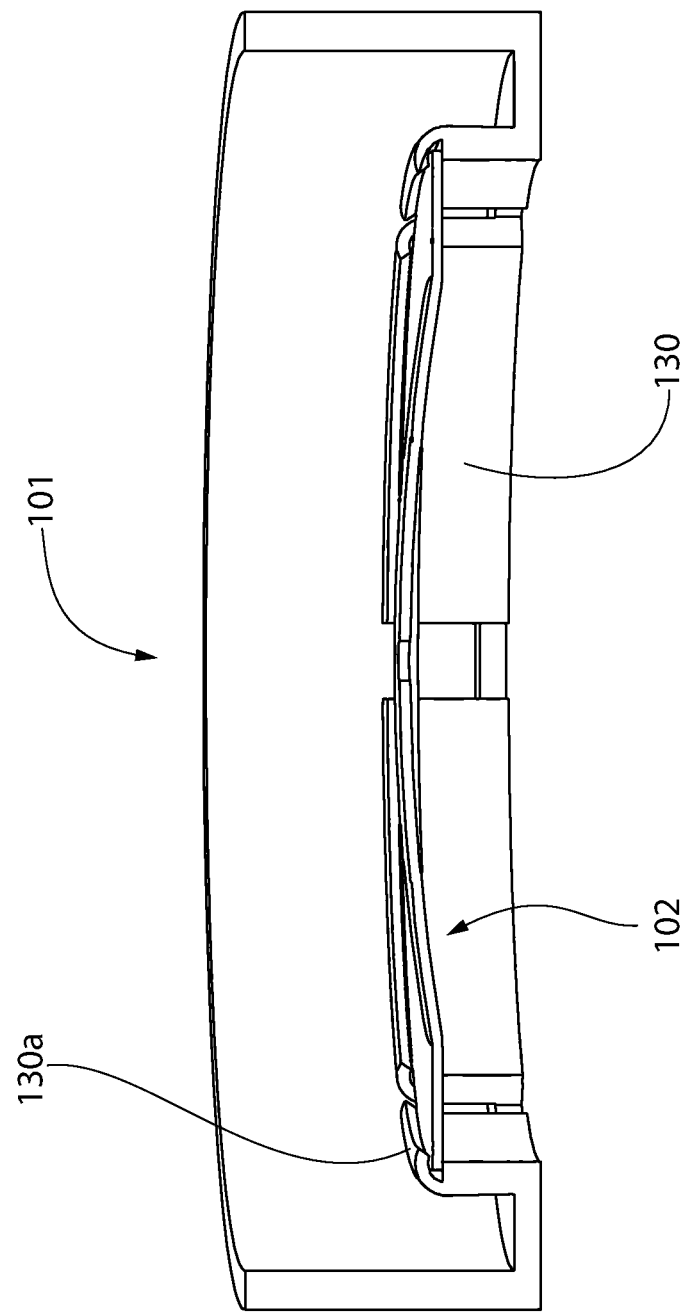
FIG. 13 is a side-elevation view of the actuator and the biasing member shown in FIG. 12.
Figure 14A:
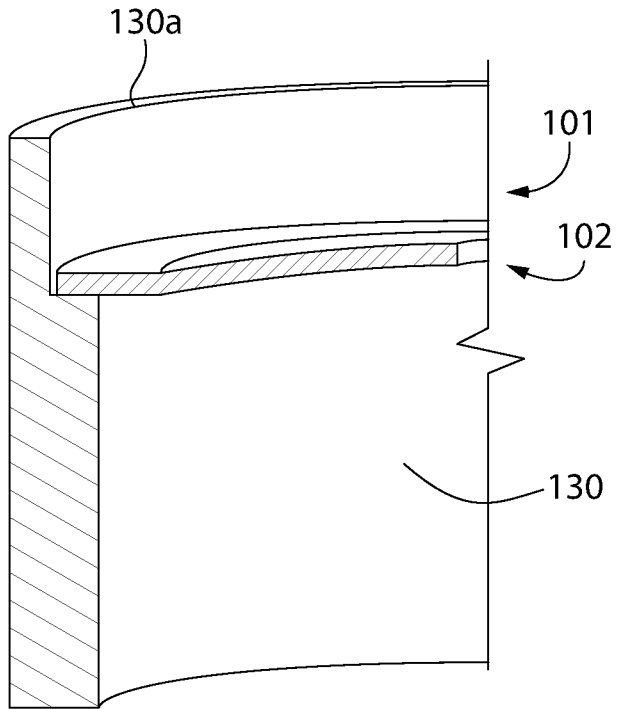
FIG. 14A is a magnified view of a portion the actuator and the biasing member of FIG. 13 shown before crimping of a portion of a ring.
Figure 14B:
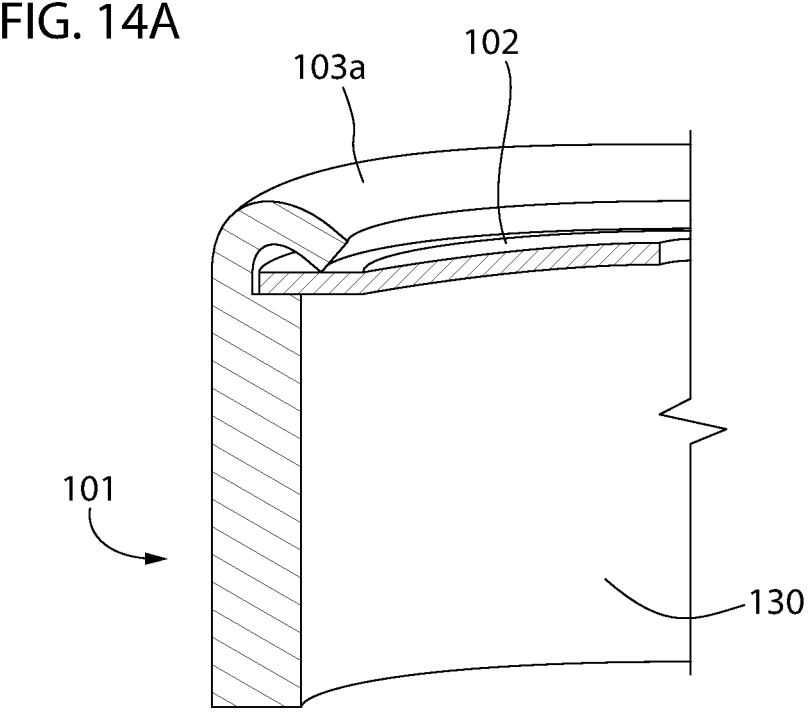
FIG. 14B is a magnified view of the same portion of the actuator and the biasing member but shown after crimping of a portion of the ring.
Figure 15:
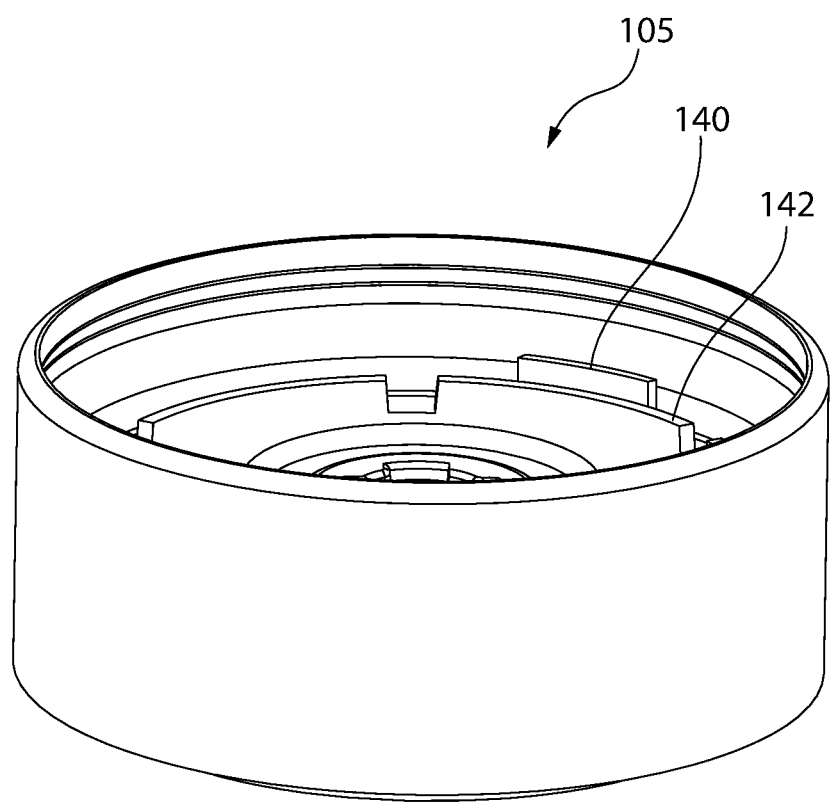
FIG. 15 is a top perspective view of a housing of one embodiment of the presently disclosed technology.
Figure 16:
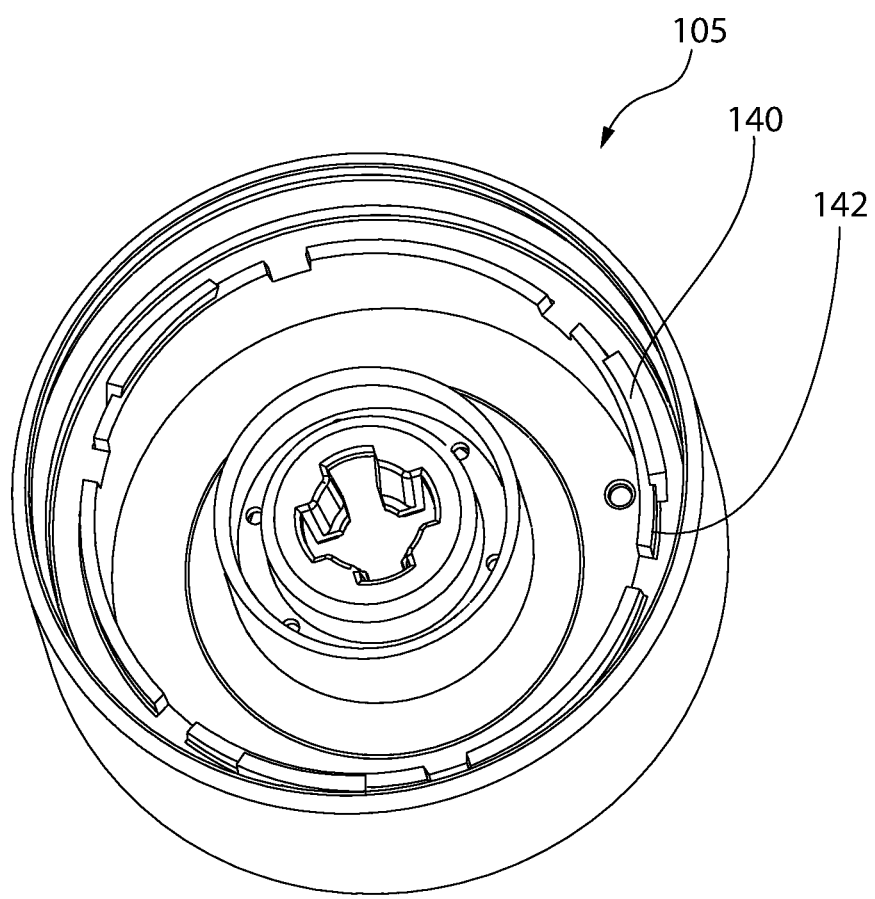
FIG. 16 is a magnified top perspective view of the housing shown in FIG. 15.

FIGS. 12-14B show at least a portion of another embodiment of the actuator 101 of the presently disclosed technology. The actuator 101 includes a rib 130 spaced radially inwardly from an outer periphery of the actuator 101. The rib 130 can be a single unitary structure that extends continuously and/or uniformly in a circle within the actuator 101. Alternatively, as shown in FIGS. 12 and 13, at least an upper or free end of the rib 130 can optionally be formed of several discrete or separate portions 130a. An upper or free edge of the rib 130 can be crimped, bent, melted, and/or welded so as to capture at least an outer edge portion of the biasing member 102 therein. Thus, in the present embodiment, the ring 3 of the earlier embodiment has been eliminated. Stated differently, crimping the biasing member can allow for a one-piece biasing member or spring instead of a two-piece biasing member or spring, which may be necessary in embodiments that do not use crimping.

Figure 26:
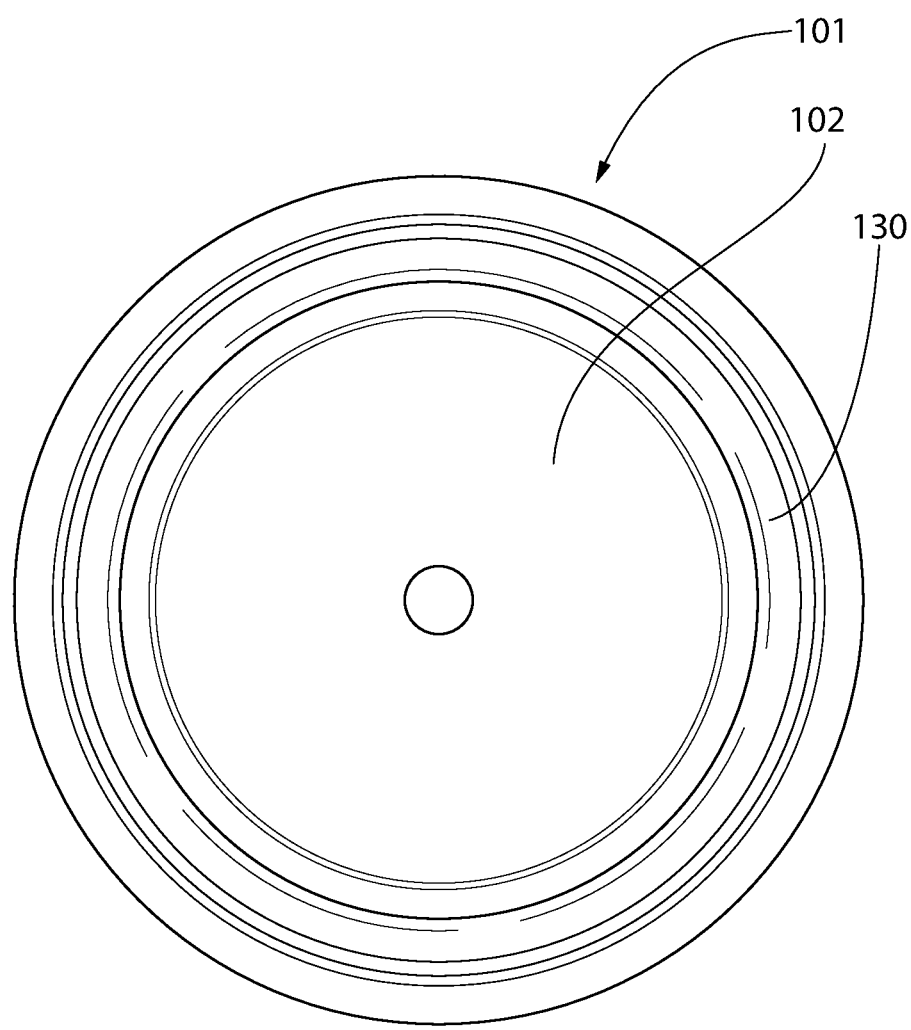
FIG. 26 is a top plan view of at least a portion of a medicament delivery system of one optional embodiment of the presently disclosed technology.

Optionally in any embodiment, it can be desirable for the bent, melted and/or welded rib 130 to be flat or at least generally flat against at least an outer periphery of a top surface of the spring 102 without any or with only limited swellings or tips, such as shown in FIG. 26. A sonotrode can be used to bend, melt and/or weld the rib.

Optionally, a distance of at least 3.45 mm can be beneficial between the top of the housing and the top of the melted rib after the ultra-sonic operation to avoid any constraints between the biasing member and the actuator. Optionally, a distance of 0.3 mm exists between the biasing member and the actuator.

Optionally, it can be beneficial to have a distance of 3.4 mm between a top of the patch holder and a top of the biasing member. In one optional embodiment, when such distance is less than 3.4 mm, there is potential contact with the actuator, which is not desirable. In one optional embodiment, when such distance is greater than 3.4 mm, there may be undesirable influence on the on the patch speed.

In one optional embodiment, the biasing member is made of Walsin SUS301 from Precison Rastal stamping. In testing, the force of the biasing member has been activated with a dynamometer with a manual slow descent of the dynamometer. The diameter of the finger used in the testing was 19 mm. Below are results of at least certain testing of such biasing members.

| Trial # | Sample # | A in mm Comparator C4 Finger Ø 1 mm | B in mm Comparator c3 Finger Ø 10 mm | Force in N 1$^{st}$ activation Finger Ø 19 mm | Force in N 2$^{nd}$ activation Finger Ø 19 mm |
|---|---|---|---|---|---|
| 1 | 38 | 3.68-.3.75 | 3.43 | 2.55 | 2.62 |
|   | 39 | 3.66-3.75 | 3.43 | 2.24 | 3.77 |
|   | 40 | 3.64-3.72 | 3.44 | 2.67 | 2.98 |
|   | 41 | 3.63-3.70 | 3.39 | 3.13 | 3.72 |
|   | 42 | 3.65 | 3.39 | 3.40 | 3.78 |
| 2 | 78 | 3.66-.3.75 | 3.40 | 3.16 | 3.11 |
|   | 79 | 3.43-3.63 | 3.24 | 3.95 |  |
|   | 80 | 3.67-3.72 | 3.42 | 3.77 |  |
|   | 81 | 3.5-3.64 | 3.34 | 4.04 |  |
|   | 82 | 3.53-3.65 | 3.35 | 3.13 |  |
| 3 | 90 | 3.49-3.52 | 3.38 | 3.86 | 3.45 |
|   | 91 | 3.52-3.71 | 3.46 | 3.40 | 3.28 |
|   | 92 | 3.48-3.58 | 3.40 | 3.29 | 2.63 (3eme) |
|   | 93 | 3.55-3.62 | 3.43 | 3.40 | 2.95 |
|   | 94 | 3.5-3.66 | 3.44 | 3.35 | 2.96 |

The distance to reach the activation force is around 1 mm. The biasing member could be activated approximately five (5) times before breaking. The above-described crimping process with an ultra-sonic machine 20 kHz produces desirable components for at least one embodiment of the presently disclosed technology. In any embodiment, it is optionally desirable to create a device with a shelf life for the patch of one year with the desiccant and a total moisture adsorption capacity of 400 mg. The ingress target for such an embodiment is 1000 μg/day. For a device with a shelf life for the patch of three years, the ingress target is preferably approximately 540 μg/day.

Figure 17A:
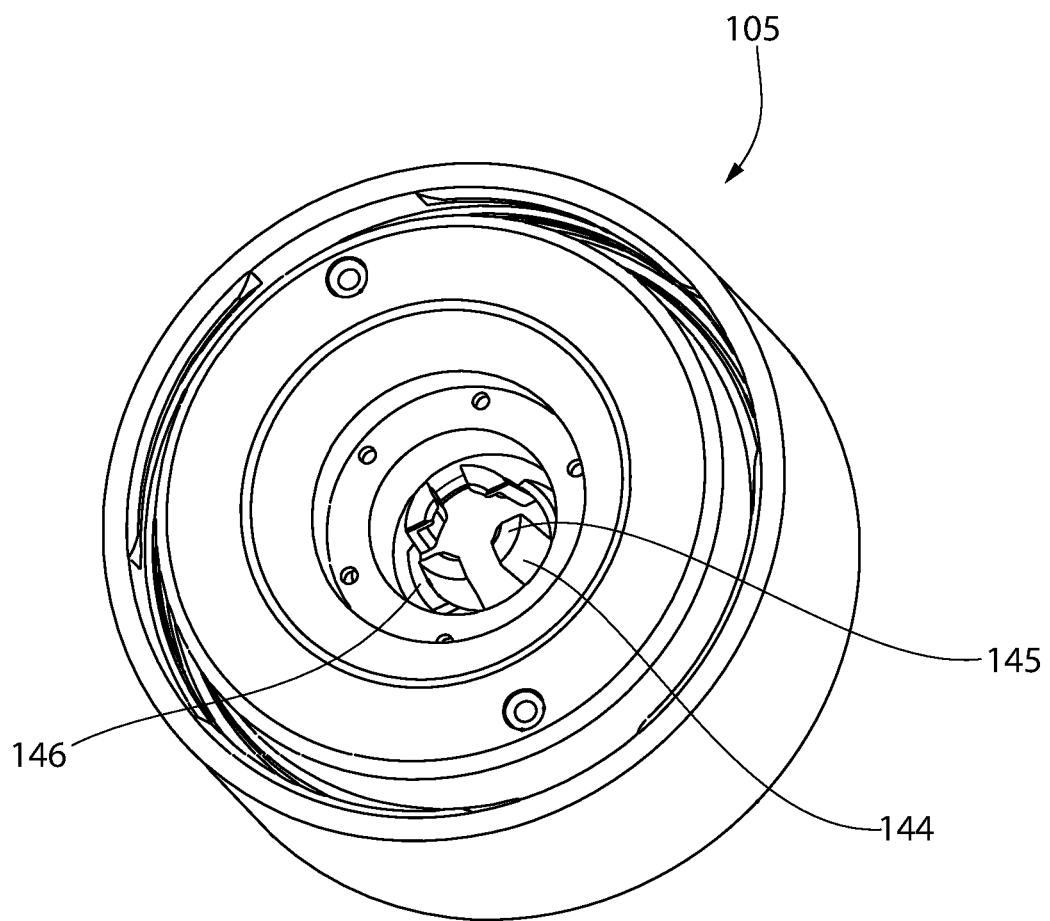
FIG. 17A is a bottom perspective view of the housing shown in FIG. 15.
Figure 17B:
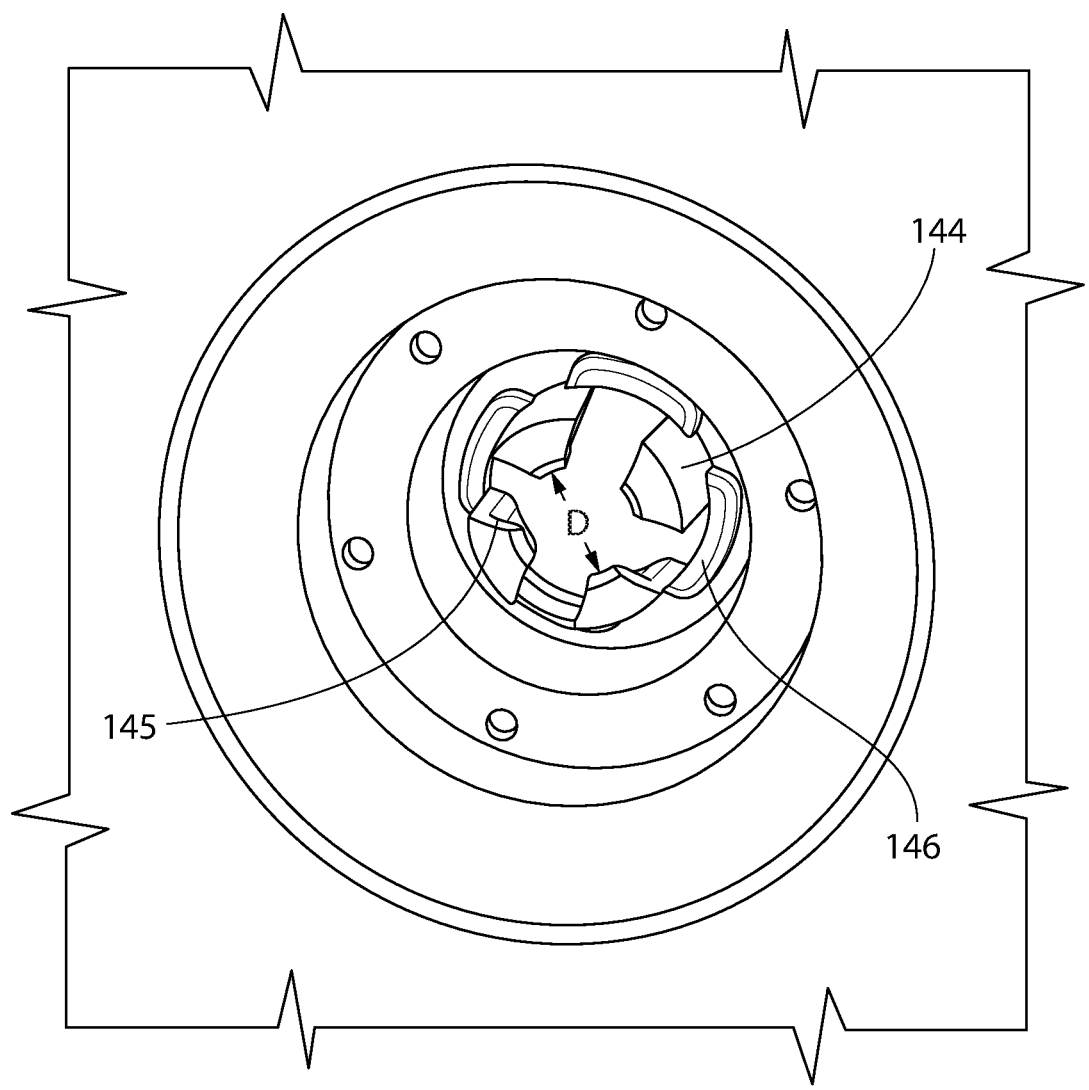
FIG. 17B is a magnified view of a portion of the housing shown in FIG. 14A.
Figure 18:
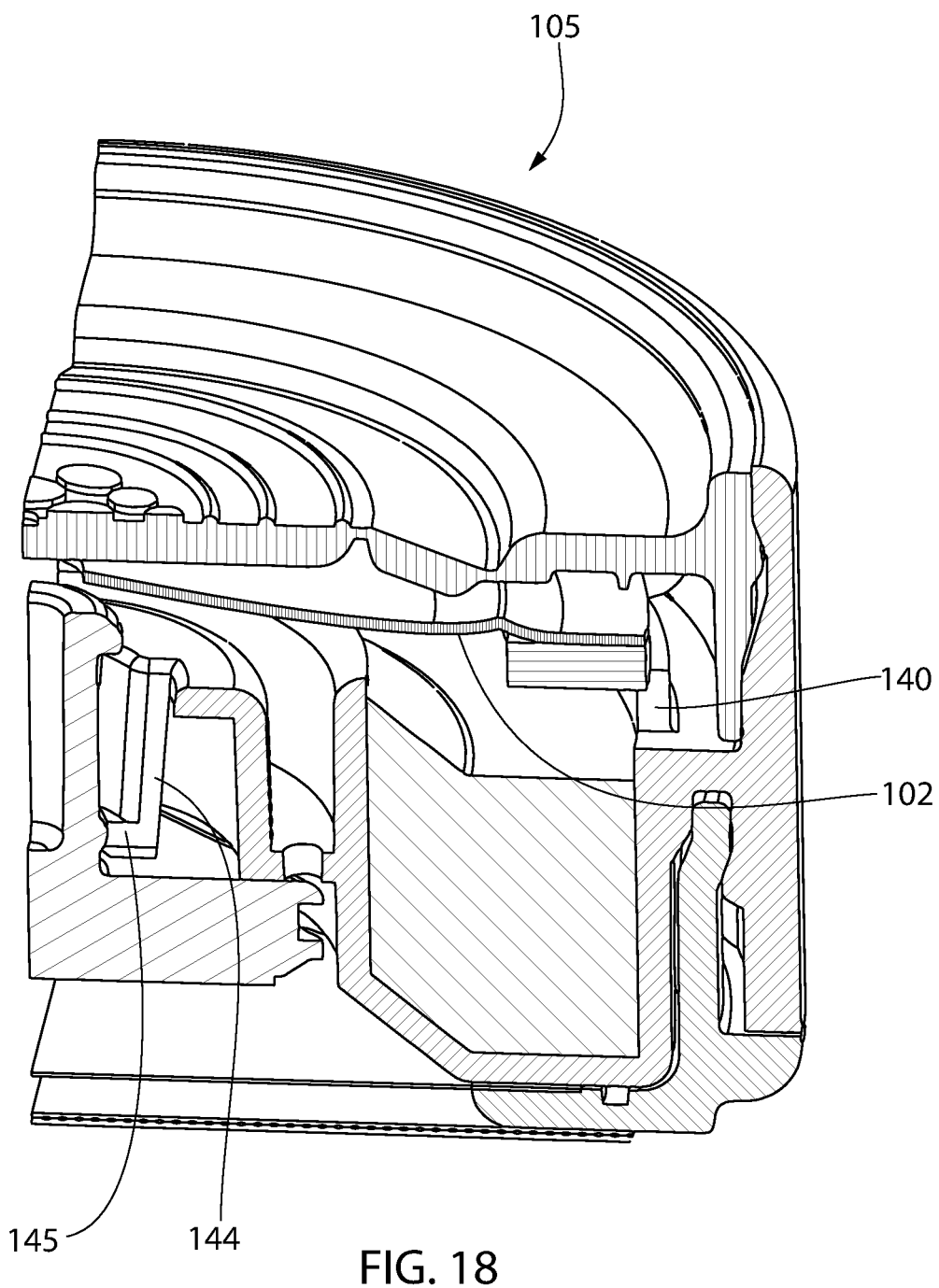
FIG. 18 is a partial cross-sectional perspective view of a portion a system employing the housing shown in FIG. 15.

FIGS. 15-18 show another embodiment of the holder or housing 105 of the presently disclosed technology. The holder 105 can include at least one or a plurality of spaced-apart ribs 140 extending upwardly toward a top of the holder 105. The ribs 140 can be sized, shaped and/or configured to center the biasing member 102 for effective use. Optionally, the holder 105 includes three spaced-apart ribs 140. An upper or free edge of each rib 140 can extend higher than or upwardly from a separation wall 142 within the holder 105. As shown in FIG. 18, the biasing member 102, the ring and/or the actuator 101 can engage or rest on the upper or free edge of each of the rib 140.

Referring to FIGS. 17A and 17B, a bottom surface or side of the holder 105 includes one or a plurality of spaced-apart legs 144. The legs 144 are designed to confine or contain the patch (not shown) within the holder 105. The legs 144 will be under tension when the patch is in the holder 105. A distal or free end of each leg 144 can include a support platform 145. The support platforms 145 can be positioned to limit the downward movement of the patch. Optionally, as shown in FIG. 17B, a distance or diameter D between opposing legs 144 (or inner surface of the support platform 145 of opposing legs 144) is exactly 3.5 mm, or in the range of 3.3-3.7 mm.

To limit the flexibility or increase the rigidity of the legs 144, a rib or support base 146 can extend at least between each adjacent pair of leg 144. Optionally, each support base 146 extends at least slightly past an edge of each of the legs 144 which it supports. Each support base 146 can be formed of a raised lip of increased thickness. The legs 144 extend further downward beyond the support bases 146. Each support base 146 can be at least slightly arcuate to conform to the same of the opening extending through the holder 105. Optionally, the support bases 146 increase the force which the legs 144 can withstand by 1.1N.

Figure 19:
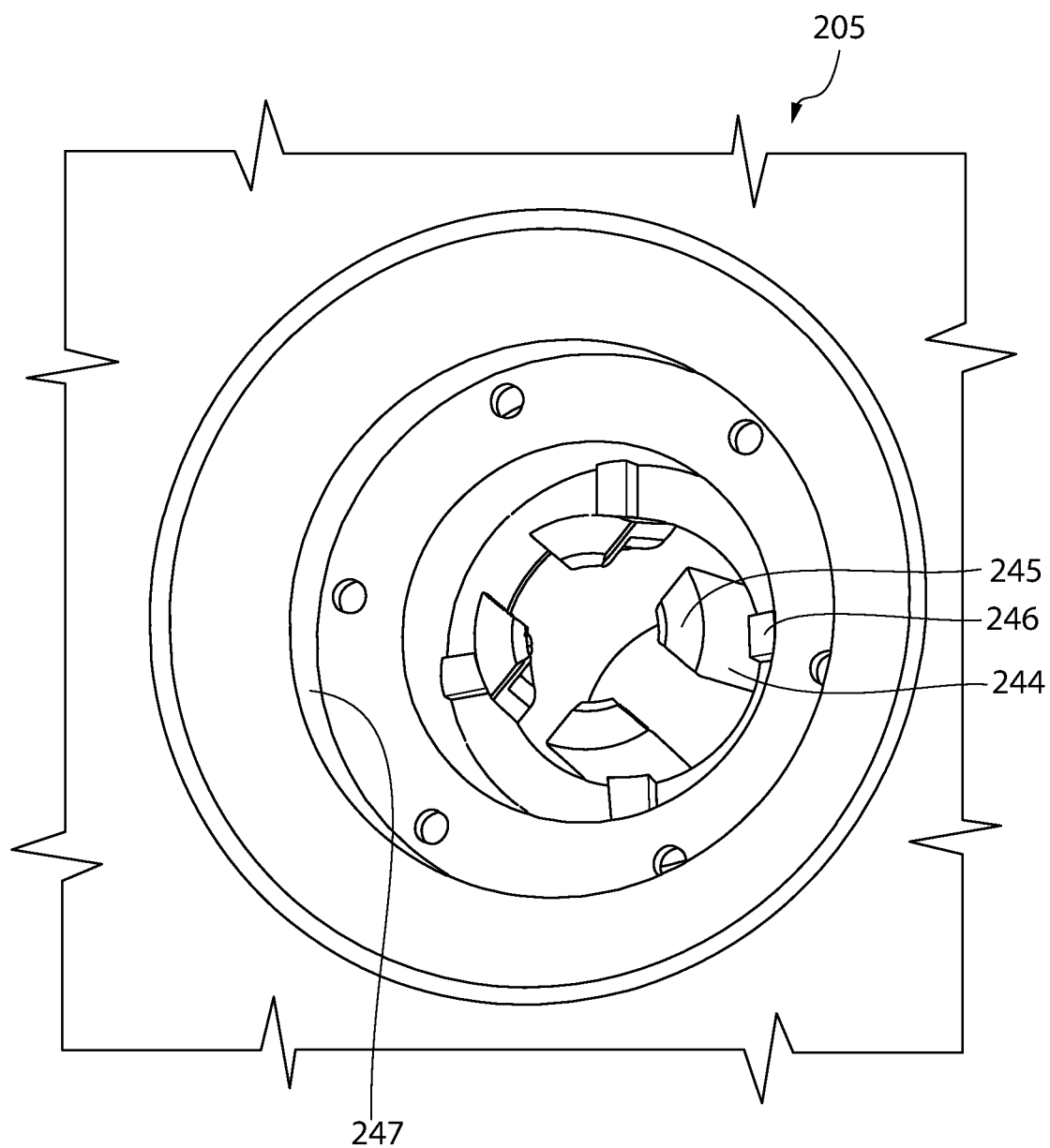
FIG. 19 is an alternative embodiment of the portion of the housing shown in FIG. 17B.
Figure 20:
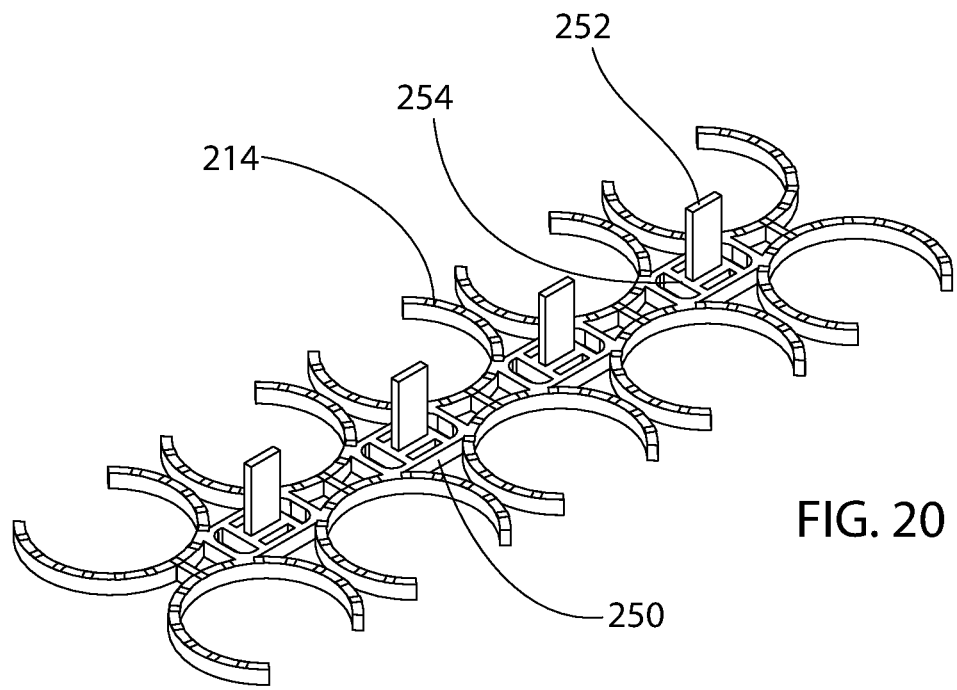
FIG. 20 is a top perspective view of a plurality of spacers according to one optional embodiment of the presently disclosed technology.
Figure 21:
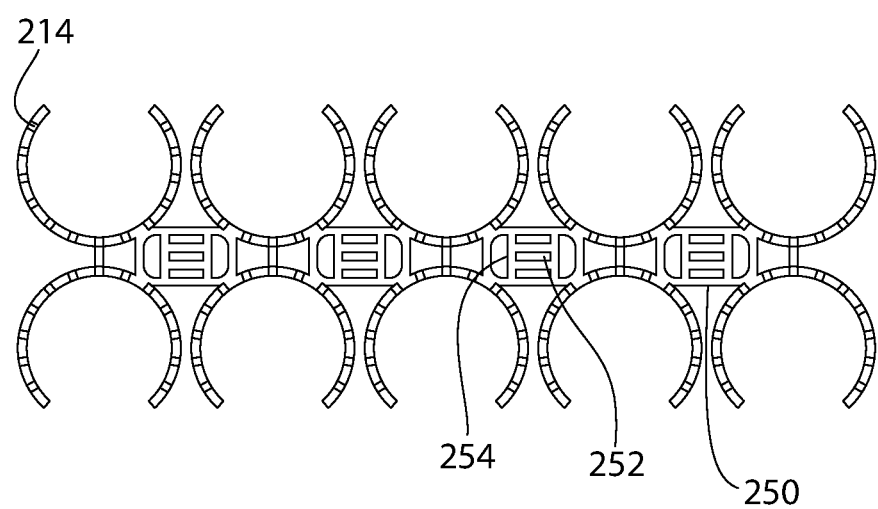
FIG. 21 is a top plan view of the plurality of spacers shown in FIG. 20.
Figure 22:
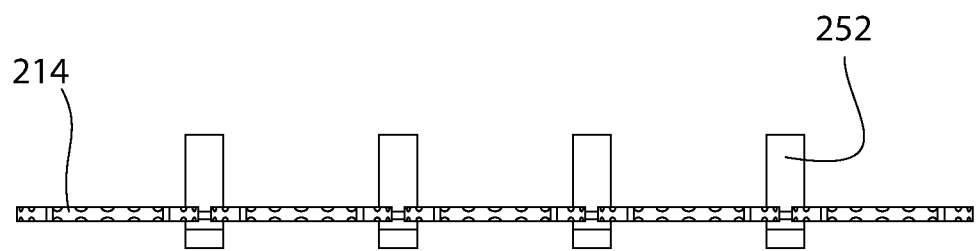
FIG. 22 is a side elevation view of the plurality of spacers shown in FIG. 20.
Figure 23:
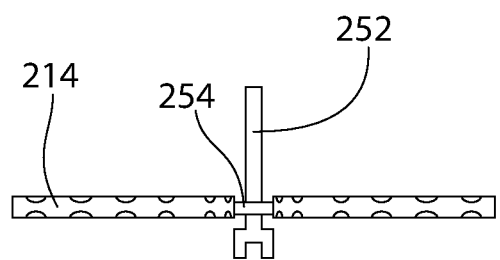
FIG. 23 is another side elevation view of the plurality of spacers shown in FIG. 20.
Figure 24:
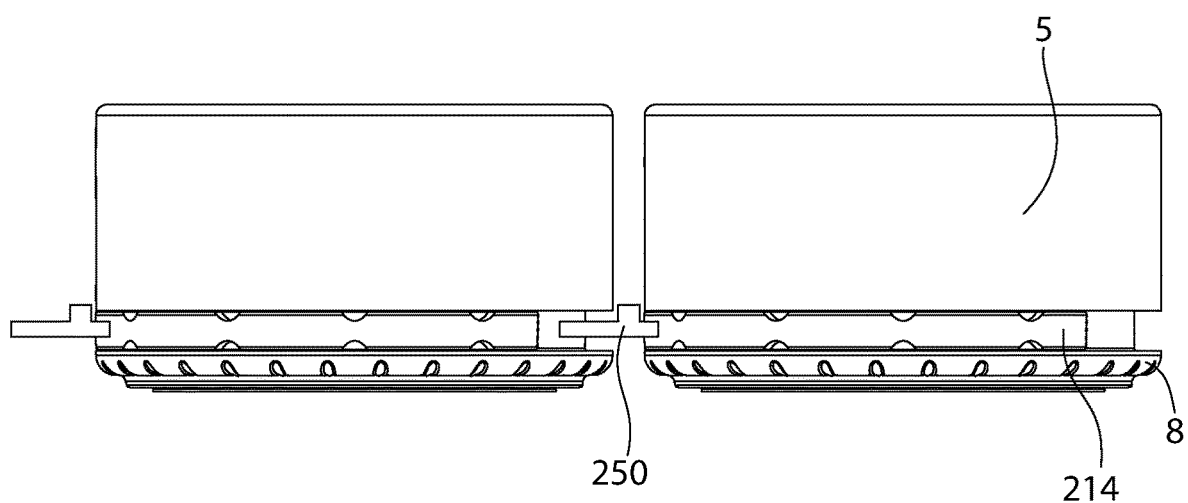
FIG. 24 is a side elevation view of two of the plurality of spacers shown in FIG. 20, wherein the spacers are separating the housing from the membrane locker of each device.

FIG. 19 shows another embodiment of the holder or housing 205 of the presently disclosed technology. Each leg 244 of the holder 205 includes a support base 246 that extends radially from the respective leg to an inner wall 247 of the housing 205. Optionally, a width of each support base 246 is less than a width of the respective leg 244.

FIGS. 20-24 show another embodiment of a holding frame or a plurality of spacers 214 of the presently disclosed technology. Each of the spacers 214 can include at least one serrated edge to aid in sterilization of the device 10. Optionally, the serrations extend around an entire perimeter of each spacer 214, which allows sterilization gas to travel into the device 10 and between two stacked devices 10. The plurality of spacers 214 can be connected by an attachment member 250. Optionally, each spacer 214 forms a portion of a semi-circle with an opening to receive at least a portion of the device 10 therein. At least one or a plurality of spaced-apart extensions 252 extend upwardly from a base 254 of the attachment member 250.

FIGS. 25A-25D show various views of an optional embodiment of a membrane assembly or locker 208 of the presently disclosed technology. In certain instances it can be beneficial to attach a film or membrane 262 to a lower opening of the membrane assembly 208. This film can be a non-irritating and non-sensitizing layer between the patch and the user's skin that can be a strong non-stick surface, but can be easily puncture it with a sharp object or point. Thus, in at least certain circumstances, it can be beneficial to secure a polymeric film or membrane to the membrane assembly 208 that, due to materials of construction, is not chemically or thermally compatible with a rigid plastic component that will be intended to be utilized.

Figure 25A:
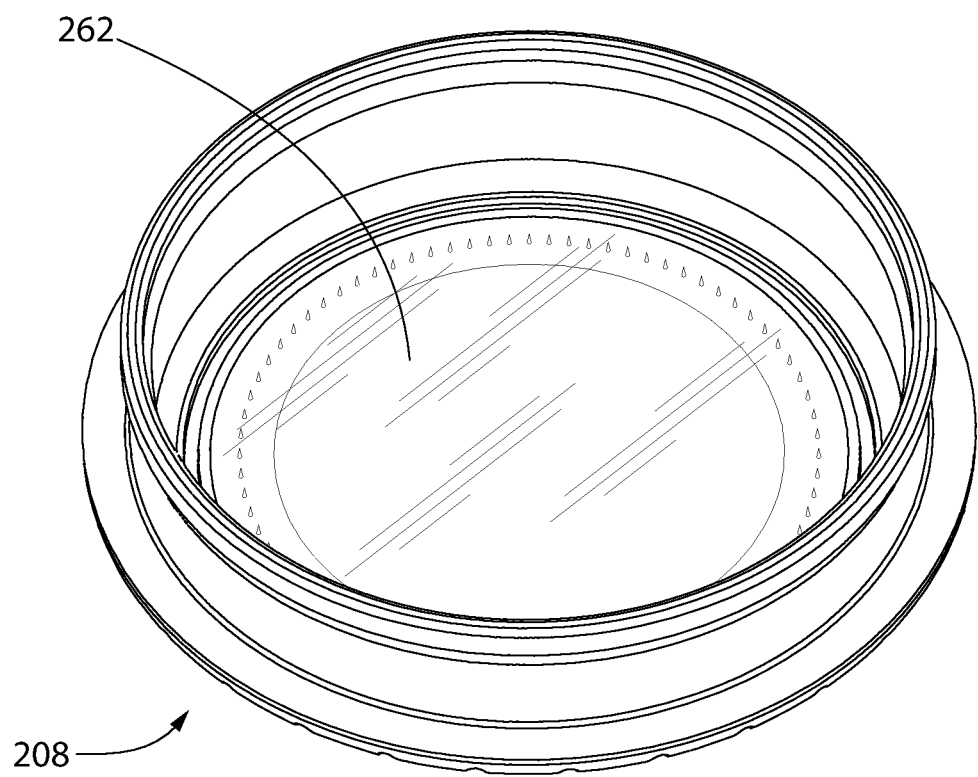
FIG. 25A is a perspective view of a membrane assembly or locker according to one embodiment of the presently disclosed technology.
Figure 25B:
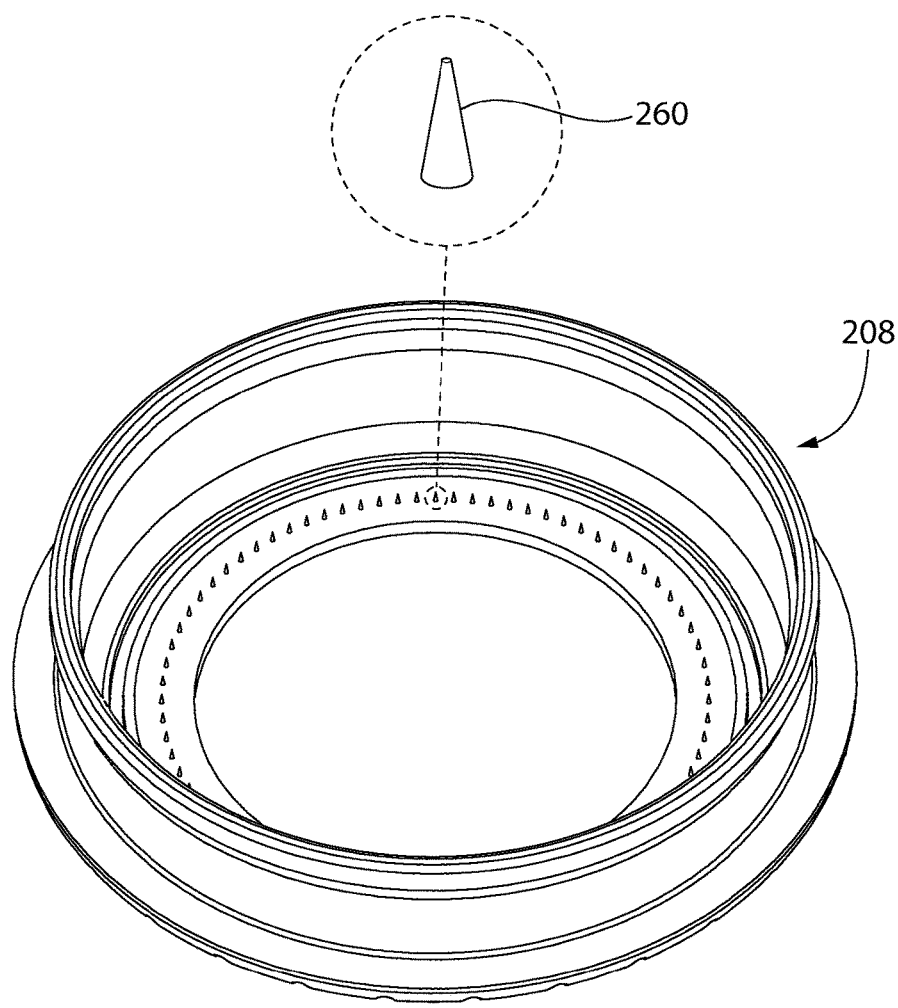
FIG. 25B is perspective view of the membrane assembly with a film omitted for clarity.
Figures 25C, 25D:
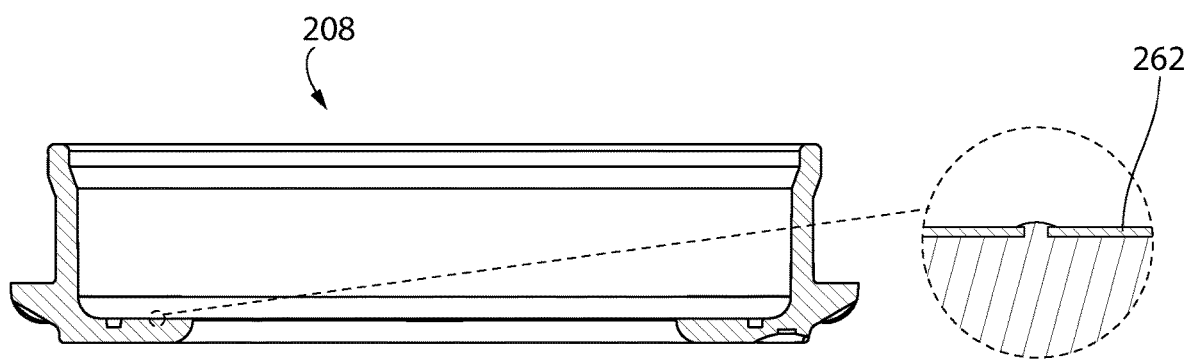
FIG. 25C is a side elevational view of the membrane assembly shown in FIG. 25A.
FIG. 25D is a magnified view of a portion of the membrane assembly shown in FIG. 25C.

Optionally, the membrane assembly 208 is a polymeric part created with means for protruding or small needle-like or nail-like protrusions or projections 260 acting as energy directors or rivets. Optionally, the projections 260 can extend upwardly from an interior surface of the membrane assembly 208. FIG. 25B reflects one embodiment of the geometry of each needle/nail like design. Optionally, each nail/needle projection 260 has sufficient draw and sharpness to allow penetration through polymeric films, such as fluorinated ethylene propylene (FEP), PFA, PTFE, having a film thickness of up to 20 microns, optionally 12-15 microns.

Optionally, the protrusions 260 are equidistantly spaced-apart to allow the film 262 to puncture through. Then, with the use of ultrasonics, a sonotrode will utilize vibrational energy to secure the polymeric film to the rigid plastic membrane assembly 208 by a creating a rivet geometry from the protrusions 260. One benefit of the equidistant spacing is that the tension force on the film 262 is equally distributed after the riveting step is completed.

In ultrasonic machining, welding and mixing, a sonotrode is a tool that creates ultrasonic vibrations and applies this vibrational energy to a gas, liquid, solid or tissue. A sonotrode usually consists of a stack of piezoelectric transducers attached to a tapering metal rod. The end of the rod is applied to the working material. An alternating current oscillating at ultrasonic frequency is applied by a separate power supply unit to the piezoelectric transducers. The current causes the transducers to expand and contract. The frequency of the current is chosen to be the resonant frequency of the tool, so the entire sonotrode acts as a half-wavelength resonator, vibrating lengthwise with standing waves at its resonant frequency. The standard frequencies used with ultrasonic sonotrodes range from 20 kHz to 70 kHz. The amplitude of the vibration is small, about 13 to 130 micrometers.

Sonotrodes are typically made of titanium, aluminum or steel, with or without heat treatment (carbide). The shape of the sonotrode (e.g., round, square, with teeth, profiled) depends on the quantity of vibratory energy and a physical constraint for a specific application. The shape of the sonotrode is optimized for the particular application. Sonotrodes of small diameter are sometimes called probes. For an ultrasonic welding or cutting application, the sonotrode gives energy directly to the welding contact area, with little diffraction. This is particularly helpful when vibrations (wave propagation) could damage surrounding electronic components.

Polymeric membranes have a thin layer of semi-permeable material that is used for solute separation as a transmembrane pressure is applied across the membrane. The degree of selectivity is largely based on the membrane charge and porosity. FEP fluoropolymer film offers the outstanding properties of FEP that can be heat sealed, thermoformed, welded, metallized, and laminated to many other materials. The FEP is often available in thickness of 0.5-20 mil. Because of the moisture absorption of FEP film is less than 0.01% when totally immersed in water, changes in relative humidity have little effect on the film. Teflon™ FEP fluoropolymer films have unusually low absorption compared with other thermoplastics. These films absorb practically no common acids or bases at temperatures as high as 200° C. (392° F.) and exposures of up to one year. Even the absorption of solvents is extremely small. Weight increases are generally less than 1% when exposed at elevated temperatures for long periods. In general, aqueous solutions are absorbed very little by film. Moisture absorption is typically less than 0.01% at ambient temperature and pressure. Unheated Teflon™ FEP fluoropolymer is essentially inert. Animal tests indicate that Teflon™ FEP is non-irritating and non-sensitizing to the skin. FEP film is very strong, but one can easily puncture it with a sharp needle-like object. FEP film or any other polymer with a very low surface energy can be used. FEP film can be an ideal non-stick layer, but for that reason does not readily bond to a surface without surface treatment (e.g., plasma or corona treatment).

In operation, to attach the film 262 to the membrane assembly 208, the film 262 is cut (e.g., with a blade or sharp edge adequate to cut around a pad) to the desired geometry to fit in the membrane assembly 208 and then overlaid onto the area that contains the projections 260. The pad (optionally made of silicone) maintains control of this film 262 as the pad has micro holes for vacuum to maintain control of the polymeric film 262 and membrane assembly 208 during movement of the silicone pad. Optionally, the silicone pad will be attached to an arm that is either manual or utilizes a robotic operation to place the polymeric film 262 over the nail/needle geometric area of the plastic membrane locker 208.

After the film 260 is in position on the membrane assembly 208, the vacuum is stopped and thus allows the membrane assembly 208 to stay in place over the protrusions 260. The silicone pad is removed from this area of operation and the sonotrode from the ultrasonic operation is placed into position over the polymeric film 260 and the membrane assembly 208, and proceeds to depress in conjunction with ultrasonic waves. This causes the polymeric film 262 to puncture through the projections 260 and then allows the projections 260 to deform to a rivet geometry, thus securing the film 262 and the membrane assembly 208 into the final position for use of the device.

Thus, the silicone pad that maintains positive control of the polymeric film 262 while it is being cut and then transported into position over the protrusions 260. The pad depresses the polymeric film 262 into its final position and then the silicone pad is removed out of this area.

The following exemplary embodiments further describe optional aspects of the presently disclosed technology and are part of this Detailed Description. These exemplary embodiments are set forth in a format substantially akin to claims (each with numerical designations followed by the letter A), although they are not technically claims of the present application. The following exemplary embodiments refer to each other in dependent relationships as "embodiments" instead of "claims."

1A. A medicament delivery device comprising:
 a housing having a top edge, an opposing bottom edge, and a longitudinal axis extending therebetween;
 desiccant positioned within the housing between the top and bottom edges;
 at least one biasing member positioned within the housing between the desiccant and the top edge of the housing; and
 a patch positioned within the housing between the biasing member and the bottom edge of the housing, at least a portion of the patch containing medicament,
 wherein activation of the biasing member causes the patch to move along the longitudinal axis to administer the medicament to a patient.

2A. The device of embodiment 1A, further comprising:
 a membrane; and
 a membrane locker positioned proximate the bottom edge of the housing, the membrane locker including a side wall, at least a portion of the side wall extending into a slot of the housing.

3A. The device of embodiment 2A, wherein the membrane locker is movable with respect to the housing.

4A. The device of any one of embodiments 1A-3A, wherein the patch is one of a microprojection array, a microarray patch, and a microarray needle.

1B. A method of making a medicament delivery system, the medicament delivery system including a housing, desiccant, a biasing member, and a membrane assembly, the membrane assembly being movable with respect to the housing between a first position and a second position, the method comprising:
 sterilizing the medicament delivery system, optionally with gas sterilization, when the membrane assembly is in the second position and a spacer is positioned within a gap between a portion of the membrane assembly and the housing;
 separating the spacer from the membrane assembly and the housing;
 separating the membrane assembly from the housing;
 inserting a patch containing medicament into the housing;
 attaching the membrane assembly to the housing;
 moving the membrane assembly from the second position to the first position such that a gap between the membrane assembly and the housing is closed; and
 inserting the sterilized medicament delivery system into packaging to maintain the sterile nature of the medicament delivery system.

2B. The method of embodiment 1B, wherein the patch is one of a microprojection array, a microarray patch, and a microarray needle.

1C. A medicament delivery device comprising:
a housing;
desiccant positioned within the housing;
at least one biasing member positioned within the housing above the desiccant; and
a patch positioned within the housing, at least a portion of the patch being surrounded by the desiccant, at least a portion of the patch containing medicament,
wherein movement of the biasing member causes the patch to move with respect to the housing to administer the medicament to a patient.

2C. The device of embodiment 1C, wherein the housing forms a cavity configured to hold the desiccant.

3C. The device of embodiment 1C, wherein the device includes a first configuration for pre-aseptic filling and a second configuration for post-aseptic filing.

4C. The device of embodiment 3C, wherein in the first configuration a gap exists between the membrane locker and the housing, the gap being configured to receive a spacer therein.

1D. A medicament delivery device comprising:
a housing defining a longitudinal axis;
desiccant positioned within the housing;
a biasing member positioned within the housing; and
a membrane locker positioned proximate the bottom edge of the housing, the membrane locker being configured to support a membrane designed to contact a user's skin, the membrane locker being movable with respect to the housing,
wherein the device includes a first configuration and a second configuration, in the first configuration a gap exists between the membrane locker and the housing, the gap being configured to receive a spacer therein.

2D. The device of embodiment 1D, wherein in the second configuration the gap is closed such that the membrane locker contacts the housing where the gap was located.

3D. The device of any one of embodiments 1D or 2D, wherein the membrane locker includes a plurality of projections.

4D. The device of embodiment 3D, further comprising a film punctured by each of the plurality of projections.

5D. The device of embodiment 4D, wherein the film is formed of fluorinated ethylene propylene (FEP) and encloses a patch within the device.

6D. The device of any one of embodiments 3D-5D, wherein ultrasound vibrations are applied to the plurality of projections.

1E. A medicament delivery device including a housing and a membrane assembly, the membrane assembly being movably attached to the housing such that a spacer is positionable between at least a portion of the membrane assembly and the housing during sterilization of the medicament delivery device, and the spacer can be separated from the membrane assembly and housing prior to use of the medicament delivery device.

2E. The device of embodiment 1E, further comprising an actuator attached to the housing, the actuator being attached to the housing at an opposite end of the housing from the membrane assembly, at least a portion of the actuator being configured to crimp a portion of a biasing member within the housing.

It will be appreciated by those skilled in the art that changes could be made to the embodiments described above without departing from the broad inventive concept thereof. It is understood, therefore, that the presently disclosed technology is not limited to the particular embodiments disclosed, but it is intended to cover modifications within the spirit and scope of the present invention as defined by the appended claims.

What is claimed is:

1. A medicament delivery device comprising:
a housing;
desiccant positioned within the housing, the desiccant having an annular shape;
a biasing member positioned within the housing above the desiccant; and
a patch positioned within the housing, at least a portion of the patch being surrounded by the desiccant, at least a portion of the patch containing medicament,
wherein movement of the biasing member causes the patch to move with respect to the housing to administer the medicament to a patient.

2. The device of claim 1, wherein the desiccant is in the form of a ring or torus.

3. The device of claim 1, further comprising:
an actuator attached to the housing above the biasing member, the actuator including a deflectable portion attached to and configured to be moveable with respect to a remainder of the actuator via one or more hinges, the deflectable portion being configured to contact the biasing member to encourage the biasing member to cause the patch to move with respect to the housing to administer the medicament to the patient.

4. The device of claim 3, wherein the actuator includes at least one rib configured to be bent over an outer edge of the biasing member.

5. The device of claim 1, further comprising:
an actuator attached to the housing above the biasing member, wherein at least a portion of the actuator is configured to crimp an outer edge of the biasing member.

6. The device of claim 1, further comprising:
a membrane locker configured to support a membrane designed to contact a user's skin, the membrane locker being attached to and configured to be movable with respect to the housing along a longitudinal axis of the housing, the membrane locker including a plurality of spaced-apart grooves around a periphery thereof, the grooves being configured to permit the passage of fluid therethrough when the device is stacked beneath a second device.

7. The device of claim 1, further comprising:
a membrane locker positioned proximate a bottom edge of the housing, the membrane locker being configured to be movable with respect to the housing between a first position and a second position, the combined housing and membrane locker being configured to receive at least a portion of a spacer therebetween when the membrane locker is in the first position.

8. The device of claim 1, wherein the device includes a first configuration for pre-aseptic filling and a second configuration for post-aseptic filing, in the first configuration a gap exists between the membrane locker and the housing, the gap being configured to receive a spacer therein.

9. The device of claim 8, wherein in the second configuration the gap is closed.

10. The device of claim 1, wherein the desiccant is formed of (i) a resin or copolymer, (ii) a channeling agent, and (iii) a molecular sieve.

11. The device of claim 1, wherein the desiccant is formed of (i) 23% by weight of PP Bormed RF830MO, (ii) 8% by weight of PEG 4000S Clamant, and (iii) 69% by weight of Molecular Sieve 4A.

12. The device of claim 1, wherein the housing includes three spaced-apart ribs extending upwardly therefrom, and wherein the ribs combine to center the biasing member within the device.

13. A medicament delivery device comprising:
a housing having a top edge, an opposing bottom edge, and a longitudinal axis extending therebetween;
desiccant positioned within the housing between the top and bottom edges;
a biasing member positioned within the housing between the desiccant and the top edge of the housing; and
a membrane locker positioned proximate the bottom edge of the housing, the membrane locker being configured to support a membrane designed to contact a user's skin, the membrane locker being movable with respect to the housing along the longitudinal axis,
wherein the device includes a first configuration for sterilization and a second configuration for delivery of medicament to a patient, in the first configuration a gap exists between the membrane locker and the housing, the gap being configured to receive a spacer therein, and wherein in the second configuration the gap is closed such that the membrane locker contacts the housing where the gap was located.

14. The device of claim 13, wherein the spacer is positioned between a portion of the membrane locker and the housing, the spacer having an arcuate shape and surrounding a portion of the membrane locker.

15. The device of claim 13, further comprising:
an actuator positioned within the housing above the biasing member, the actuator including a projection extending outwardly from a bottom surface of the actuator, the projection being received in an opening of the biasing member.

16. The device of claim 13, wherein the desiccant has an annular shape or is in the form of a torus.

17. The device of claim 13, wherein the desiccant is formed of (i) a resin or copolymer, (ii) a channeling agent, and (iii) a molecular sieve.

18. The device of claim 13, wherein the desiccant is formed of (i) 23% by weight of PP Bormed RF830MO, (ii) 8% by weight of PEG 4000S Clariant, and (iii) 69% by weight of Molecular Sieve 4A.

19. The device of claim 13, wherein the housing includes three spaced-apart ribs extending upwardly therefrom, and wherein the ribs combine to center the biasing member within the device.

20. A method of making a medicament delivery system, the medicament delivery system including a housing, desiccant, a biasing member, and a membrane assembly, the membrane assembly being movable with respect to the housing between a first position and a second position, the method comprising:
sterilizing the medicament delivery system when the membrane assembly is in the first position and a spacer is positioned within a gap between a portion of the membrane assembly and the housing; and
inserting the sterilized medicament delivery system into packaging to maintain a sterile environment for the medicament delivery system.

21. The method of claim 20, further comprising:
removing the sterilized medicament delivery system from the packaging;
removing the spacer from the medicament delivery system;
removing the membrane assembly from the housing;
inserting a patch containing medicament into the housing; and
reattaching the membrane assembly to the housing to enclose the patch within the medicament delivery system.

22. The method of claim 20, wherein the following occurs prior to inserting the sterilized medicament delivery system into packaging:
separating the spacer from the membrane assembly and the housing;
separating the membrane assembly from the housing;
inserting a patch containing medicament into the housing;
attaching the membrane assembly to the housing; and
moving the membrane assembly from the second position to the first position such that a gap between the membrane assembly and the housing is closed.

23. The method of claim 20, wherein the membrane assembly includes a plurality of projections, the membrane assembly being attached to a film, each of the plurality of projections puncturing the film, the method further comprising:
applying ultrasound vibrations to at least one of the projections.

* * * * *

UNITED STATES PATENT AND TRADEMARK OFFICE
CERTIFICATE OF CORRECTION

| | |
|---|---|
| PATENT NO. | : 11,878,136 B2 |
| APPLICATION NO. | : 16/949458 |
| DATED | : January 23, 2024 |
| INVENTOR(S) | : Jean-Pierre Giraud et al. |

It is certified that error appears in the above-identified patent and that said Letters Patent is hereby corrected as shown below:

In the Claims

Column 15, Claim 11, Lines 1-4, replace "The device of claim 1, wherein the desiccant is formed of (i) 23% by weight of PP Bormed RF830MO, (ii) 8% by weight of PEG 4000S Clamant, and (iii) 69% by weight of Molecular Sieve 4A." with --The device of claim 1, wherein the the desiccant is formed of (i) 23% by weight of PP Bormed RF830MO, (ii) 8% by weight of PEG 4000S Clariant, and (iii) 69% by weight of Molecular Sieve 4A.--

Signed and Sealed this
Twenty-sixth Day of March, 2024

Katherine Kelly Vidal
*Director of the United States Patent and Trademark Office*